(12) United States Patent
Oost et al.

(10) Patent No.: US 8,703,775 B2
(45) Date of Patent: *Apr. 22, 2014

(54) AMIDOMETHYL-SUBSTITUTED OXINDOLE DERIVATIVES AND THE USE THEREOF FOR THE TREATMENT OF VASOPRESSIN-DEPENDENT ILLNESSES

(75) Inventors: Thorsten Oost, Biberach an der Riss (DE); Astrid Netz, Ludwigshafen (DE); Herve Geneste, Ludwigshafen (DE); Wilfried Braje, Ludwigshafen (DE); Wolfgang Wernet, Ludwigshafen (DE); Andrea Hager-Wernet, legal representative, Neustadt (DE); Liliane Unger, Ludwigshafen (DE); Wilfried Hornberger, Ludwigshafen (DE); Wilfried Lubisch, Ludwigshafen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/746,700

(22) PCT Filed: Dec. 5, 2008

(86) PCT No.: PCT/EP2008/066931
§ 371 (c)(1),
(2), (4) Date: Nov. 29, 2010

(87) PCT Pub. No.: WO2009/071687
PCT Pub. Date: Jun. 11, 2009

(65) Prior Publication Data
US 2011/0077253 A1   Mar. 31, 2011

Related U.S. Application Data

(60) Provisional application No. 61/012,241, filed on Dec. 7, 2007.

(51) Int. Cl.
*A61K 31/496* (2006.01)
*A61K 31/4545* (2006.01)
*C07D 401/14* (2006.01)

(52) U.S. Cl.
USPC ....... 514/253.09; 514/316; 544/364; 546/187

(58) Field of Classification Search
None
See application file for complete search history.

(56) References Cited

U.S. PATENT DOCUMENTS

| | | | |
|---|---|---|---|
| 3,964,896 A | 6/1976 | Brouwer et al. |
| 4,022,901 A | 5/1977 | Narayanan et al. |
| 4,122,257 A | 10/1978 | Prossel et al. |
| 5,594,023 A | 1/1997 | Wagnon et al. |
| 5,914,328 A | 6/1999 | Lin et al. |
| 5,948,793 A | 9/1999 | Abreo et al. |
| 5,977,144 A | 11/1999 | Meyer et al. |
| 6,090,818 A | 7/2000 | Foulon et al. |
| 6,130,217 A | 10/2000 | Arnold et al. |
| 6,207,863 B1 | 3/2001 | Berrier et al. |
| 6,538,003 B1 | 3/2003 | Galli et al. |
| 6,579,880 B2 | 6/2003 | Weidner-Wells et al. |
| 6,596,732 B2 | 7/2003 | Serradeil-Le-Gal et al. |
| 6,605,610 B1 | 8/2003 | Coe et al. |
| 6,624,164 B2 | 9/2003 | Schoentjes et al. |
| 6,809,105 B2 | 10/2004 | Schrimpf et al. |
| 6,833,370 B1 | 12/2004 | Schrimpf et al. |
| 6,864,277 B2 | 3/2005 | Roux et al. |
| 6,919,359 B2 | 7/2005 | Piotrowski et al. |
| 7,041,685 B2 | 5/2006 | Cai et al. |
| 7,119,086 B2 | 10/2006 | Di Malta et al. |
| 7,902,379 B2 | 3/2011 | Lubisch et al. |
| 8,017,631 B2 | 9/2011 | Dahl et al. |
| 8,129,389 B2 | 3/2012 | Lubisch et al. |
| 8,350,055 B2 | 1/2013 | Oost et al. |
| 2003/0109545 A1 | 6/2003 | Serradeil-Le-Gal et al. |
| 2003/0114683 A1 | 6/2003 | Roux et al. |
| 2003/0139413 A1 | 7/2003 | Schoentjes et al. |
| 2003/0162767 A1 | 8/2003 | Roux et al. |
| 2004/0063601 A1 | 4/2004 | Denome et al. |
| 2004/0152724 A1 | 8/2004 | Dart et al. |
| 2004/0180878 A1* | 9/2004 | Di Malta et al. ............. 514/218 |
| 2004/0186107 A1 | 9/2004 | Schrimpf et al. |
| 2004/0204461 A1 | 10/2004 | Karp et al. |
| 2005/0070718 A1* | 3/2005 | Lubisch et al. ............. 548/181 |
| 2006/0019976 A1 | 1/2006 | Karp et al. |
| 2007/0021465 A1 | 1/2007 | Al-Abed et al. |
| 2007/0021607 A1 | 1/2007 | Lubisch et al. |
| 2007/0185126 A1 | 8/2007 | Lubisch et al. |
| 2008/0167286 A1 | 7/2008 | Gopalakrishnan et al. |
| 2008/0255203 A1 | 10/2008 | Lee et al. |

(Continued)

FOREIGN PATENT DOCUMENTS

CA   2107348 A1   7/1993
CA   2593044 A1   7/2006

(Continued)

OTHER PUBLICATIONS

Banker et al. "Modern Pharmaceutics", 3rd Ed. p. 596 (1996).*
Wolff, Manfred E. Burger's Medicinal Chemistry, 5th Ed. Part 1, pp. 975-977 (1995).*
Thibonnier, Exp.OPin.Invest.Drugs, vol. 7(5), p. 729-740 (1998).*
Hays, New England Journal of Medicine, vol. 355(20), p. 2146-2148 (2006).*
Itoh et al. Am. J. Physiol. Endocrinol. Metab.vol. 291, p. E147-E151 (2006).*
Emsley, R.A., et al., "Vasopressin secretion and memory impairment in alcoholic Korsakoff's Syndrome," Alcohol & Alcoholism, vol. 30, No. 2, pp. 223-229, 1995.
Everts, H.G.J., et al., "Differential modulation of lateral septal vasopressin receptor blockade in spatial learning, social recognition, and anxiety-related behaviors in rats," Behavioural Brain Research 99 (1999), pp. 7-16.

(Continued)

*Primary Examiner* — Emily Bernhardt
(74) *Attorney, Agent, or Firm* — Lisa V. Mueller; Michael Best & Friedrich LLP

(57) ABSTRACT

The present invention relates to novel amidomethyl-substituted oxindole derivatives, pharmaceutical compositions comprising them, and their use for the treatment of vasopressin-dependent disorders.

14 Claims, No Drawings

(56) References Cited

U.S. PATENT DOCUMENTS

| | | |
|---|---|---|
| 2008/0269236 A1 | 10/2008 | Ji et al. |
| 2008/0318923 A1 | 12/2008 | Sekiguchi et al. |
| 2009/0005397 A1 | 1/2009 | Lubisch et al. |
| 2009/0163492 A1 | 6/2009 | Oost et al. |
| 2009/0215790 A1 | 8/2009 | Lubisch et al. |
| 2010/0305086 A1 | 12/2010 | Gopalakrishnan et al. |
| 2011/0077241 A1 | 3/2011 | Lubisch et al. |
| 2011/0124658 A1 | 5/2011 | Netz et al. |
| 2011/0190314 A1 | 8/2011 | Gopalakrishnan et al. |

FOREIGN PATENT DOCUMENTS

| | | |
|---|---|---|
| DE | 10148598 A1 | 10/2002 |
| EP | 0979814 B1 | 10/2003 |
| EP | 2226074 A2 | 9/2010 |
| EP | 2101763 B1 | 7/2012 |
| EP | 2114921 B1 | 12/2012 |
| EP | 2546250 A1 | 1/2013 |
| EP | 2546251 A1 | 1/2013 |
| EP | 2546252 A1 | 1/2013 |
| WO | 9313083 A1 | 7/1993 |
| WO | 9315051 A | 8/1993 |
| WO | 9518105 A | 7/1995 |
| WO | 9640682 A1 | 12/1996 |
| WO | 9825901 A | 6/1998 |
| WO | 9910338 A2 | 3/1999 |
| WO | 9932480 A1 | 7/1999 |
| WO | 9965876 A1 | 12/1999 |
| WO | 0007600 A1 | 2/2000 |
| WO | 0045799 A2 | 8/2000 |
| WO | 0071534 A1 | 11/2000 |
| WO | 0075110 A1 | 12/2000 |
| WO | 0155130 A | 8/2001 |
| WO | 0155134 A | 8/2001 |
| WO | 0162736 A1 | 8/2001 |
| WO | 0164668 A | 9/2001 |
| WO | 0181334 A2 | 11/2001 |
| WO | 0181347 A2 | 11/2001 |
| WO | 0187295 A1 | 11/2001 |
| WO | 0198295 A | 12/2001 |
| WO | 02068417 A2 | 9/2002 |
| WO | 02100826 A2 | 12/2002 |
| WO | 03008407 A | 1/2003 |
| WO | 2004018607 A2 | 3/2004 |
| WO | 2005/030755 A | 4/2005 |
| WO | 2006/005609 A | 1/2006 |
| WO | 2006047392 A2 | 5/2006 |
| WO | 2006071184 A1 | 7/2006 |
| WO | 2006072458 A2 | 7/2006 |
| WO | 2006086068 A1 | 8/2006 |
| WO | 2006096358 A1 | 9/2006 |
| WO | 2006100080 A1 | 9/2006 |
| WO | 2006100081 A2 | 9/2006 |
| WO | 2006100082 A2 | 9/2006 |
| WO | 2006114400 A1 | 11/2006 |
| WO | 2007149395 A2 | 12/2007 |
| WO | 2008028903 A2 | 3/2008 |
| WO | 2008073942 A2 | 6/2008 |
| WO | 2008/080970 * | 7/2008 |
| WO | 2008/080971 * | 7/2008 |
| WO | 2008/080972 * | 7/2008 |
| WO | 2008/080973 * | 7/2008 |
| WO | 2009148452 A1 | 12/2009 |
| WO | 2010138600 A2 | 12/2010 |
| WO | 2010148598 A1 | 12/2010 |

OTHER PUBLICATIONS

Maturi, M.F., et al., "Coronary vasoconstriction induced by vasopressin. Production of myardial ischemia in dogs by constriction of nondiseased small vessels," Circulation, 83, pp. 2111-2121, 1991.

Oshikawa, S., et al., "Vasopressin stimulates insulin release from islet cells through V1b receptors: a combined pharmacological/knockout approach," Molecular Pharmacology, vol. 65, No. 3, pp. 623-629, 2004.

Pavo, I., et al., "Vasopressin deficiency decreases the frequency of gastroduodenal ulceration in humans," J. Physiol. (Paris) 94 (2000), pp. 63-66.

Scheurer, M.A., et al., "Vasopressin to attenuate pulmonary hypertension and improve systemic blood pressure after correction of obstructed total anomalous pulmonary venous return," The Journal of Thoracic and Cardiovascular Surgery, Feb. 2005, pp. 464-466.

Griebel, et al., Proc. Natl. Acad. Sci., 2002, 99(9), pp. 6370-6375.

Japundžić-Žigon et al., J. Pharmacol. Sci. 95, pp. 47-55, 2004.

Lee, et al., Am. Heart J. 2003; 146:9-18.

Ring, R.H., Current Pharmaceutical Design, 2005, 11, pp. 205-225.

Kocsis, et al., Invest. Radiol. 1987; 22:973-977.

Yatagai, et al., Eur. J. Endocrinol. 2003, 148:221-226.

Jonat, et al., Arch. Dis. Child 1999, 81:57-59.

Thibonnier, et al., Current Opinion in Pharmacology 2003, 3:683-687.

Kocsis, et al., Br. J. exp. Path. (1987) 68, 35-43.

Cheung, et al., J. Clin. Pharmacol. 1994; 34:664-670.

Grant, et al., Clinical Science (1985) 69, pp. 471-476.

Banfi L., et al., "Ugi Multicomponent Reaction Followed by an Intermolecular Nucleophilic Substitution: Convergent Multicomponent Synthesis of 1-sulfonyl 1,4-diazepan-5-ones and of their Benzo-Fuzed Derivatives," Journal of Organic Chemistry, 2007, vol. 72 (6), pp. 2151-2160.

Barberis C., et al., "Structural Bases of Vasopressin/oxytocin Receptor Function," Journal of Endocrinology, 1998, vol. 156 (2), pp. 223-239.

Bitner R.S., et al., "Reduced Nicotinic Receptor-Mediated Antinociception Following in Vivo Antisense Knock-Down in Rat," Brain Research, 2000, vol. 871, pp. 66-74.

Brain C.T., et al., "Novel Procedure for the Synthesis of 1,3,4-oxadiazoles from 1,2-diacylhydrazines Using Polymer-Supported Burgess Reagent Under Microwave Conditions," Tetrahedron Letters, 1999, vol. 40, pp. 3275-3278.

Bundgaard, E. et al., "Design of Prodrugs, Elsevier Science Publishers, Amsterdam, Table of Contents," 1986.

Bundgaard H., ed., in: Design of Prodrugs, Elsevier Science, 1985, Table of Contents.

Chaplan S.R., et al., "Quantitative Assessment of Tactile Allodynia in the Rat Paw," Journal of Neuroscience Methods, 1994, vol. 53 (1), pp. 55-63.

Chattopadhyay S.K., et al., "Formation of Medium-Ring Heterocycles by Diene and Enyne Metathesis," Tetrahedron, 2007, vol. 63, pp. 3919-3952.

Co-pending U.S. Appl. No. 61/058,735, filed Jun. 4, 2008.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Cucchiaro G., et al., "The Dorsal Raphe Nucleus as a Site of Action of the Antinociceptive and Behavioral Effects of the Alpha4 Nicotinic Receptor Agonist Epibatidine," Journal of Pharmacology and Experimental Therapeutics, 2005, vol. 313 (1), pp. 389-394.

Curtis L., et al., "Potentiation of Human Alpha4beta2 Neuronal Nicotinic Acetylcholine Receptor by Estradiol," Molecular Pharmacology, 2002, vol. 61 (1), pp. 127-135.

De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.

De Francesco R., et al., "Challenges and Successes in Developing New Therapies for Hepatitis C," Nature, 2005, vol. 436 (7053), pp. 953-960.

Decker M.W., et al., "Nicotinic Acetylcholine Receptor Agonists: a Potential New Class of Analgesics," Current Topics in Medicinal Chemistry, 2004, vol. 4 (3), pp. 369-384.

Decker M.W., et al., "The Therapeutic Potential of Nicotinic Acetylcholine Receptor Agonists for Pain Control," Expert Opinion on Investigational Drugs, 2001, vol. 10 (10), pp. 1819-1830.

Diaz G.J., et al., "The [3H]dofetilide Binding Assay is a Predictive Screening Tool for hERG Blockade and Proarrhythmia: Comparison

(56) References Cited

OTHER PUBLICATIONS of Intact Cell and Membrane Preparations and Effects of Altering [K+]o," Journal of Pharmacological and Toxicological Methods, 2004, vol. 50 (3), pp. 187-199.
Dorwold F.Z., "Side Reactions in Organic Synthesis," Wiley-VCH, 2005, Preface.
Dunbar G.C., et al., "Effect of Ispronicline, a Neuronal Nicotinic Acetylcholine Receptor Partial Agonist, in Subjects with Age Associated Memory Impairment (AAMI).," Journal of Psychopharmacology, 2007, vol. 21 (2), pp. 171-178.
Ersek K., et al., "The Cognitive Effects of Opioids," Pain Management Nursing, 2004, vol. 5 (2), pp. 75-93.
Ettmayer P., et al., "Lessons Learned from Marketed and Investigational Prodrugs," Journal Medicinal Chemistry, 2004, vol. 47 (10), pp. 2393-2404.
European Search Report for Application No. EP10163998, mailed on Jan. 28, 2011, 5 pages.
European Search Report for Application No. EP12177640, mailed on Dec. 12, 2012, 2 pages.
European Search Report for Application No. EP12177642, mailed on Dec. 12, 2012, 2 pages.
European Search Report for Application No. EP12177644, mailed on Dec. 12, 2012, 1 page.
Ex Parte Quayle Action mailed Sep. 11, 2008 for U.S. Appl. No. 10/574,211, filed Jan. 22, 2007.
Ex Parte Quayle Action mailed Aug. 21, 2012 for U.S. Appl. No. 12/839,612, filed Jul. 20, 2010.
Ex Parte Quayle Action mailed Aug. 22, 2012 for U.S. Appl. No. 12/134,678, filed Jun. 6, 2008.
Ferreira M., et al., "Brainstem Nicotinic Receptor Subtypes That Influence Intragastric and Arterial Blood Pressures," Journal of Pharmacology and Experimental Therapeutics, 2000, vol. 294 (1), pp. 230-238.
Final Office Action mailed May 10, 2012 for U.S. Appl. No. 12/746,715, filed Dec. 7, 2010.
Final Office Action mailed Feb. 13, 2012 for U.S. Appl. No. 12/746,688, filed Nov. 29, 2010.
Final Office Action mailed Mar. 26, 2013 for U.S. Appl. No. 12/746,688, filed Nov. 29, 2010.
Final Office Action mailed Apr. 27, 2012 for U.S. Appl. No. 12/521,713, filed Sep. 7, 2010.
Final Office Action mailed Feb. 27, 2012 for U.S. Appl. No. 12/746,707, filed Dec. 7, 2010.
Final Office Action mailed Sep. 27, 2012 for U.S. Appl. No. 13/080,071, filed Apr. 5, 2011.
Final Office Action mailed Sep. 29, 2011 for U.S. Appl. No. 12/787,937, filed May 26, 2010.
Franklin S. R., et al., "Positive Allosteric Modulation of Alpha $ Beta 2 Nicotinic Receptors Potrntiates Some CNS Effects of the Alpha 4 Beta 2 Agonist, ABT-594," Biochemical Pharmacology, 2009, vol. 78 (7), pp. 921.
Freshney R.I., et al., Culture of Animal Cells, A Manual of Basic Technique, 1983, Wiley & Sons, Inc., pp. 7-9.
Furniss B.S., et al., Vogel's Textbook of Practical Organic Chemistry, 5th Edition, Longman Scientific & Technical, 1989, Table of Contents.
Gopalakrishnan, M. et al., "Ion channels—Ligand gated. Comprehensive Medicinal Chemistry II, Edited by Triggle D.J. et al..," Major Reference Works, 2006, Unit 2.22, pp. 877-918, Elsevier.
Greene T.W., et al., in: Protective Groups in Organic Synthesis, 3rd Edition, John Wiley and Sons, Inc., 1999, Preface, Table of Contents, Abbreviations.
Greene T.W., et al., "Protection for the Amino group," Protective Groups in Organic Synthesis, 1999, Third Edition, pp. 494-653.
Higuchi T., et al., eds., Pro-drugs as Novels Delivery Systems, vol. 14, ACS Symposium Series, 1975, Table of Contents.
Hulme C., et al., "Quaternary Substituted PDE4 Inhibitors I: the Synthesis and in Vitro Evaluation of a Novel Series of Oxindoles," Bioorganic & Medicinal Chemistry Letters, 1998, vol. 8 (2), pp. 175-178.

Humphrey G.R., et al., "A Novel Synthesis of 3-Bromo-1,2,4-oxadiazoles," Journal of Heterocyclic Chemistry, 1989, vol. 26 (1), pp. 23-24.
International Preliminary Report on Patentability and Written Opinion for Application No. PCT/US08/066002, mailed on Dec. 6, 2010, 8 pages.
International Preliminary Report on Patentability and Written Opinion for Application No. PCT/US2007/087090, mailed on Jun. 16, 2009, 11 pages.
International Preliminary Report on Patentability and Written Opinion for Application No. PCT/US2010/036213, mailed on Nov. 29, 2011, 14 pages.
International Search Report for Application No. PCT/EP2008/066934, mailed on Jun. 4, 2009, 6 pages.
International Search Report for Application No. PCT/EP2008/066935 (WO2009/071690), mailed on Jun. 4, 2009, 6 pages.
International Search Report for Application No. PCT/US08/066002, mailed on Jan. 20, 2009, 3 pages.
International Search Report for Application No. PCT/US2007/087090, mailed on Oct. 20, 2008, 5 pages.
International Search Report for Application No. PCT/US2007/087091, mailed on May 8, 2008, 3 pages.
International Search Report for Application No. PCT/US2010/036213, mailed on Nov. 24, 2010, 8 pages.
Isobe T., et al., "2-Chloro-1,3-dimethylimidazolinium Chloride. 1. A Powerful Dehydrating Equivalent to DCC," The Journal of Organic Chemistry, 1999, vol. 64, pp. 6984-6988.
Khan I.M., et al., "Ablation of Primary Afferent Terminals Reduces Nicotinic Receptor Expression and the Nociceptive Responses to Nicotinic Agonists in the Spinal Cord," Journal of Neurocytology, 2004, vol. 33 (5), pp. 543-556.
Khan M.T., et al., "Structure-Activity Relationships of Tyrosinase Inhibitory Combinatorial Library of 2,5-Disubstituted-1,3,4-Oxadiazole Analogues," Bioorganic & Medicinal Chemistry, 2005, vol. 13 (10), pp. 3385-3395.
Kim S.H., et al., "An Experimental Model for Peripheral Neuropathy Produced by Segmental Spinal Nerve Ligation in the Rat," Pain, 1992, vol. 50 (3), pp. 355-363.
Kirrane T., et al., "Effects of Amphetamine on Cognitive Impairment in Schizotypal Personality Disorder," Biological Psychiatry, 1996, vol. 39 (7), pp. 581.
Kocevar M., et al., "Ring Transformations of Some 4-Aminopteridine 3-Oxides and Derivatives," Tetrahedron, 1982, vol. 39 (5), pp. 823-829.
Koch Uwe et al., "2-(2-thieny1)-5,6-dihydroxy-4-carboxypyri midines as inhibitors of the hepatitis C virus NS5B polymerase: Discovery, SAR, modeling, and mutagenesis," Journal of Medicinal Chemistry, vol. 49(5), pp. 1693-1705, 2006.
Lauretti G.R., "Highlights in Opioid Agonists and Antagonists," Neurotherapeutics, 2006, vol. 6 (4), pp. 613-622.
Lin Y., et al., "New Synthesis of 1,2,4-Triazoles and 1,2,4-Oxadiazoles," The Journal of Organic Chemistry, 1979, vol. 44 (23), pp. 4160-4164.
Lynch J.J., et al., "ABT-594 (A Nicotinic Acetylcholine Agonist): Anti-allodynia in a Rat Chemotherapy-induced Pain Model," European Journal of Pharmacology, 2005, vol. 509 (1), pp. 43-48.
March J., "Advanced Organic Chemistry: Reactions, Mechanisms, and Structure" 3rd Edition, John Wilsey & Sons, 1985, Table of Contents.
Mark N.F., et al., "Kirk-Othmer Encyclopedia of Chemical Technology" Second Completely Revised Edition, John Wiley & Sons Inc., 1972, Table of Contents.
Marubio L.M., et al., "Reduced Antinociception in Mice Lacking Neuronal Nicotinic Receptor Subunits," Nature, 1999, vol. 398 (6730), pp. 805-810.
McClelland R.A., "Kinetics and Mechanism of Amide Acetal Hydrolysis," Journal of the American Chemical Society, 1978, vol. 100 (6), pp. 1844-1849.
Nakamura I., et al., "Transition-Metal-Catalyzed Reactions in Heterocyclic Synthesis," Chemical Reviews, 2004, vol. 104 (5), pp. 2127-2198.

(56) References Cited

OTHER PUBLICATIONS

Narahashi T., et al., "Mechanisms of Action of Cognitive Enhancers on Neuroreceptors," Biological & Pharmaceutical Bulletin, 2004, vol. 27 (11), pp. 1701-1706.
Non-Final Office Action mailed Oct. 1, 2012 for U.S. Appl. No. 12/746,707, filed Dec. 7, 2010.
Non-Final Office Action mailed Mar. 2, 2012 for U.S. Appl. No. 12/134,678, filed Jun. 6, 2008.
Non-Final Office Action mailed Aug. 4, 2009 for U.S. Appl. No. 11/440,569, filed May 25, 2006.
Non-Final Office Action mailed Jun. 5, 2009 for U.S. Appl. No. 10/574,211, filed Jan. 22, 2007.
Non-Final Office Action mailed Dec. 9, 2008 for U.S. Appl. No. 11/440,569, filed May 25, 2006.
Non-Final Office Action mailed Dec. 9, 2010 for U.S. Appl. No. 11/953,625, filed Dec. 10, 2007.
Non-Final Office Action mailed Jan. 10, 2012 for U.S. Appl. No. 12/839,612, filed Jul. 20, 2010.
Non-Final Office Action mailed Feb. 11, 2013 for U.S. Appl. No. 13/590,261, filed Aug. 21, 2012.
Non-Final Office Action mailed Oct. 12, 2012 for U.S. Appl. No. 12/746,688, filed Nov. 29, 2010.
Non-Final Office Action mailed Apr. 15, 2011 for U.S. Appl. No. 12/134,678, filed Jun. 6, 2008.
Non-Final Office Action mailed Apr. 18, 2011 for U.S. Appl. No. 12/787,937, filed May 26, 2010.
Non-Final Office Action mailed Aug. 19, 2011 for U.S. Appl. No. 12/521,713, filed Sep. 7, 2010.
Non-Final Office Action mailed Mar. 19, 2012 for U.S. Appl. No. 13/080,071, filed Apr. 5, 2011.
Non-Final Office Action mailed Jan. 22, 2009 for U.S. Appl. No. 10/574,211, filed Jan. 22, 2007.
Non-Final Office Action mailed Jul. 22, 2011 for U.S. Appl. No. 12/746,688, filed Nov. 29, 2010.
Non-Final Office Action mailed Jul. 22, 2011 for U.S. Appl. No. 12/746,707, filed Dec. 7, 2010.
Non-Final Office Action mailed Feb. 24, 2012 for U.S. Appl. No. 12/839,595, filed Jul. 20, 2010.
Non-Final Office Action mailed Aug. 30 2011 for U.S. Appl. No. 12/746,715, filed Dec. 7, 2010.
Non-Final Office Action mailed Nov. 30, 2010 for U.S. Appl. No. 10/574,211, filed Jan. 22, 2007.
Non-Final Office Action mailed Sep. 30, 2011 for U.S. Appl. No. 12/134,678, filed Jun. 6, 2008.
Notice of Allowance mailed Oct. 1, 2010 for U.S. Appl. No. 11/440,569, filed May 25, 2006.
Notice of Allowance mailed Dec. 2, 2009 for U.S. Appl. No. 10/574,211, filed Jan. 22, 2007.
Notice of Allowance mailed Sep. 4, 2012 for U.S. Appl. No. 12/839,612, filed Jul. 20, 2010.
Notice of Allowance mailed May 5, 2010 for U.S. Appl. No. 10/574,211, filed Jan. 22, 2007.
Notice of Allowance mailed Dec. 10, 2012 for U.S. Appl. No. 12/134,678, filed Jun. 6, 2008.
Notice of Allowance mailed Jan. 10, 2011 for U.S. Appl. No. 10/574,211, filed Jan. 22, 2007.
Notice of Allowance mailed Jul. 10, 2012 for U.S. Appl. No. 12/521,713, filed Sep. 7, 2010.
Notice of Allowance mailed Mar. 12, 2010 for U.S. Appl. No. 11/440,569, filed May 25, 2006.
Notice of Allowance mailed Nov. 13, 2012 for U.S. Appl. No. 12/521,713, filed Sep. 7, 2010.
Notice of Allowance mailed Jun. 24, 2010 for U.S. Appl. No. 11/440,569, filed May 25, 2006.
Notice of Allowance mailed Jun. 26, 2012 for U.S. Appl. No. 12/839,595, filed Jul. 20, 2010.
Office action mailed Dec. 1, 2011 for European Application No. 08770247.8 filed Jun. 6, 2008.
Office action mailed Sep. 10, 2012 for European Application No. 10720520.5 filed May 26, 2010.
Office action mailed Nov. 17, 2011 for European Application No. 10163998.7 filed Dec. 12, 2007.
Office action mailed Jun. 18, 2012 for European Application No. 10163998.7 filed Dec. 12, 2007.
Office action mailed Mar. 29, 2012 for European Application No. 08770247.8 filed Jun. 6, 2008.
Pasternak G.W., "Pharmacological Mechanisms of Opioid Analgesics," Clinical Neuropharmacology, 1993, vol. 16 (1), pp. 1-18.
Poulain R.F., et al., "Parallel Synthesis of 1,2,4-oxadiazoles from carboxylic Acids Using an Improved, Uronium-based Activation," Tetrahedron Letters, 2001, vol. 42 (8), pp. 1495-1498.
Prescott D.M., "Methods in Cell Biology", Academic Press, 1976, Table of Contents.
Qian X., et al., "Syntheses and Insecticidal Activities of Novel 2,5-Disubstituted- 1,3,4-Oxadiazoles," Journal of Chemical Technology and Biotechnology, 1996, vol. 67 (2), pp. 124-130.
Rashid M.H., et al., "Tonic Inhibitory Role of Alpha4beta2 Subtype of Nicotinic Acetylcholine Receptors on Nociceptive Transmission in The Spinal Cord in Mice," Pain, 2006, vol. 125 (1-2), pp. 125-135.
Reynaud P. et al., "A New Synthetic Route to 1,3,4-oxadiazoles. Pharmacological Study of Some New Derivatives", Journal of Heterocyclic Chemistry, 1992, vol. 29 (4), pp. 991-993.
Roche E.B., ed., Bioreversible Carries in Drug Design Theory and Application, Pergamon Press, 1987, Table of Contents.
Rueter L.E., et al., "Abt-089: Pharmacological Properties of a Neuronal Nicotinic Acetylcholine Receptor Agonist for the Potential Treatment of Cognitive Disorders," CNS Drug Review, 2004, vol. 10 (2), pp. 167-182.
Ryckmans T., et al., "Modulation of the Vasopressin System for the Treatment of CNS Diseases," Current opinion in drug discovery & development, 2010, vol. 13 (5), pp. 538-547.
Serradeil-Le Gal C., et al., "Characterization of (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist," Journal of Pharmacology and Experimental Therapeutics, 2002, vol. 300 (3), pp. 1122-1130.
Skoubis P.D., et al., "Mapping Brain Activity Following Administration of a Nicotinic Acetylcholine Receptor Agonist, ABT-594, Using Functional Magnetic Resonance Imaging In Awake Rats," Neuroscience, 2006, vol. 137 (2), pp. 583-591.
Smalley S.L., "Genetic Influences in Childhood-Onset Psychiatric Disorders: Autism and Attention-Deficit/hyperactivity Disorder," American Journal of Human Genetics, 1997, vol. 60 (6), pp. 1276-1282.
Sobol E., et al., "Tetramethylcyclopropyl Analogue of A Leading Antiepileptic Drug, Valproic Acid. Synthesis and Evaluation of Anticonvulsant Activity of Its Amide Derivatives," Journal of Medicinal Chemistry, 2004, vol. 47 (17), pp. 4316-4326.
Stella V.J., "Prodrugs as Therapeutics," Expert Opinion on Therapeutic Patents, 2004, vol. 14 (3), pp. 277-280.
Street L.J., et al., "Synthesis and Serotonergic Activity of 5-(0xadiazolyl)tryptamines: Patent Agonists for 5-HTID Receptors," Journal of Medicinal Chemistry, 1993, vol. 36 (11), pp. 1529-1538.
Supplementary Partial European Search Report for Application No. 08770247, mailed on Mar. 16, 2012, 4 pages.
Testa B., et al., "Prodrug Research: Futile or Fertile?," Biochemical Pharmacology, 2004, vol. 68, pp. 2097-2106.
Venkatesh S., et al., "Role of the Development Scientist in Compound Lead Selection and Optimization," Journal of Pharmaceutical Sciences, 2000, vol. 89 (2), pp. 145-154.
Wakefield B., Fluorinated Pharmaceuticals, Innovations in Pharmaceutical Technology, 2000, pp. 74-78.
Wang Y., et al., "A Simple and Effcient One Step Synthesis of 1,3,4-Oxadiazoles Utilizing Polymer-Supported Reagents and Microwave Heating," Tetrahedron Letters, 2006, vol. 47 (1), pp. 105-108.
Webster M., "Ninth New Collegiate Dictionary" Definition of Prevention, Springfield, Massachusetts, 2000, pp. 933.
Wersinger S.R., et al., "Vasopressin V1b Receptor Knockout Reduces Aggressive Behavior in Male Mice," Molecular Psychiatry , 2002, vol. 7 (9), pp. 975-984.

(56) References Cited

OTHER PUBLICATIONS

Wiffen P.J., et al., Gabapentin for Acute and Chronic Pain (Review), Cochrane Database of Systematic Reviews, 2005, vol. 20 (3), pp. 1-23.

Wilens T.E., et al., "ABT-089, A Neuronal Nicotinic Receptor Partial Agonist, for the Treatment of Attention-Deficit/Hyperactivity Disorder in Adults: Results of a Pilot Study," Biological Psychiatry, 2006, vol. 59 (11), pp. 1065-1070.

International Search Report from International Application Publication No. WO 2009/071687 A1.

Final Office Action mailed Apr. 19, 2013 for U.S. Appl. No. 12/746707, filed Dec. 7, 2010.

Notice of Allowance mailed Jun. 11, 2013 for U.S. Appl. No. 12/839,595, filed Jul. 20, 2010.

Notice of Allowance mailed Apr. 15, 2013 for U.S. Appl. No. 12/746,688, filed Nov. 29, 2010.

Notice of Allowance mailed Jun. 25, 2013 for U.S. Appl. No. 12/521,713, filed Sep. 7, 2010.

Notice of Allowance mailed May 28, 2013 for U.S. Appl. No. 12/746,715, filed Dec. 7, 2010.

Bonte, J.P. et al., "Acyl-6 benzoxazolinones (1 er memoire)," European Journal of Medicinal Chemistry (1974) 9 (5):491-496.

Final Office Action mailed Dec. 3, 2012 for U.S. Appl. No. 13/361,488, filed Jan. 30, 2012.

Final Rejection mailed Oct. 10, 2013 for U.S. Appl. No. 13/590,261, filed Aug. 21, 2012.

Griebel G., et al., "The Vasopressin V1b Receptor as a Therapeutic Target in Stress-Related Disorders," Current Drug Targets. CNS and Neurological Disorders, 2003, vol. 2 (3), pp. 191-200.

Non-Final Office Action mailed Aug. 1, 2013 for U.S. Appl. No. 12/521,713, filed Sep. 7, 2010.

Non-Final Office Action mailed Oct. 8, 2013 for U.S. Appl. No. 13/080,071, filed Apr. 5, 2011.

Non-Final Office Action mailed Jul. 20, 2012 for U.S. Appl. No. 13/361,488, filed Jan. 30, 2012.

Office action mailed Aug. 1, 2013 for European Application No. 10163998.7 filed Dec. 12, 2007.

Final Office Action mailed Nov. 22, 2013 for U.S. Appl. No. 12/746,707, filed Dec. 7, 2010.

Notice of Allowance mailed Dec. 6, 2013 for U.S. Appl. No. 12/521,713, filed Sep. 7, 2010.

Notice of Allowance mailed Nov. 25, 2013 for U.S. Appl. No. 12/746,688, filed Nov. 29, 2010.

* cited by examiner

AMIDOMETHYL-SUBSTITUTED OXINDOLE DERIVATIVES AND THE USE THEREOF FOR THE TREATMENT OF VASOPRESSIN-DEPENDENT ILLNESSES

CROSS-REFERENCE TO RELATED APPLICATIONS

This is the U.S. national stage entry of International Patent Application No. PCT/EP2008/066931, filed on Dec. 5, 2008, which claims priority to U.S. Provisional Patent Application No. 61/012,241, filed Dec. 7, 2007, the contents of all of which are hereby incorporated by reference.

The present invention relates to novel substituted oxindole derivatives, pharmaceutical compositions comprising them, and their use for the treatment of vasopressin-dependent disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3 and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740).

Novel substituted oxindoles having a phenylsulfonyl group in position 1 are described herein. 1-Phenylsulfonyl-1,3-dihydro-2H-indol-2-ones have previously been described as ligands of vasopressin receptors. WO 93/15051, WO 95/18105, WO 98/25901, WO 01/55130, WO 01/55134, WO 01/164668 and WO 01/98295 also describe derivatives having arylsulfonyl groups in position 1 of the oxindole structure. These compounds differ from the compounds of the invention essentially through the substituents in position 3.

Thus, WO 93/15051 and WO 98/25901 describe 1-phenylsulfonyl-1,3-dihydro-2H-indol-2-ones, in which the oxindole structure is substituted in position 3 by two alkyl radicals which may also together form a cycloalkyl radical (spiro linkage), as ligands of vasopressin receptors. As alternative, the spiro ring may comprise heteroatoms such as oxygen and nitrogen (optionally with substituents).

WO 95/18105 describes 1-phenylsulfonyl-1,3-dihydro-2H-indol-2-ones having a nitrogen atom in position 3 as ligands of vasopressin receptors. In addition, radicals selected from optionally substituted alkyl, cycloalkyl, phenyl or benzyl radicals are bonded in position 3.

WO 03/008407 describes 1-phenylsulfonyloxindoles in which pyridylpiperazines are linked via an oxycarbonyl group to the oxindole in position 3.

WO 2006/005609 describes 1-phenylsulfonyloxindoles in which 4-(4-propylpiperazin-1-yl)piperidine residues are linked via a 2-oxoethyl group to the oxindole in position 3, for example 1-(2,4-dimethoxyphenylsulfonyl)-3-(2-ethoxyphenyl)-2-oxo-3-{2-oxo-2-[4-(4-propylpiperazin-1-yl)piperidin-1-yl]-2,3-dihydro-1H-indole-5-carbonitrile (example 194).

Besides the binding affinity for the vasopressin V1b receptor, further properties may be advantageous for the treatment and/or prophylaxis of vasopressin-dependent disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)"). A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)"). A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)"). A larger quotient Ki(OT)/Ki(V1b) means a greater V1b selectivity.

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/ml);

7.) suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $ng \cdot h \cdot l^{-1}$), oral bioavailability, (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-dependent diseases. The compounds were intended to have a high activity and selectivity, especially a high affinity and selectivity vis-à-vis the vasopressin V1b receptor. In addition, the substance of the invention was intended to have one or more of the aforementioned advantages 1.) to 8.).

The object is achieved by compounds of the formula I (I)

in which
$R^1$ is hydrogen, methoxy or ethoxy;
$R^2$ is hydrogen or methoxy;
$R^3$ is hydrogen, methyl, ethyl, n-propyl or isopropyl;
$X^1$ and $X^2$ are N or CH, with the proviso that $X^1$ and $X^2$ are not simultaneously N;
and by their pharmaceutically acceptable salts and prodrugs thereof.

Accordingly, the present invention relates to compounds of the formula I (also "compounds I" hereinafter) and the pharmaceutically acceptable salts of the compounds I and the prodrugs of the compounds I.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhäuser Verlag, vol. 10, pp. 224-285. These include for example hydrochloric acid, citric acid, tartaric acid, lactic acid, phosphoric acid, methanesulfonic acid, acetic acid, formic acid, maleic acid and fumaric acid.

The term "prodrugs" means compounds which are metabolized in vivo to the compounds I of the invention. Typical examples of prodrugs are described in C. G. Wermeth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example compounds I in which the outer nitrogen atom of the outer piperidine/piperazine ring forms an amide/peptide linkage by this nitrogen atom being substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an amino acid residue linked via CO, e.g. glycine, alanine, serine, phenylalanine and the like linked via CO, in the position of the radical $R^3$. Further suitable prodrugs are alkylcarbonyloxyalkyl carbamates in which the outer nitrogen atom of the outer piperidine/piperazine ring has in the position of the radical $R^3$ a group of the formula —C(=O)—O—CHR$^a$—O—C(=O)—R$^b$ in which R$^a$ and R$^b$ are independently of one another $C_1$-$C_4$-alkyl. Such carbamates are described for example in J. Alexander, R. Cargill, S. R. Michelson, H. Schwam, J. Medicinal Chem. 1988, 31(2), 318-322. These groups can then be eliminated under metabolic conditions and result in compounds I in which $R^3$ is H.

$C_1$-$C_4$-Alkyl is in the context of the present invention a linear or branched alkyl radical having 1 to 4 carbon atoms, such as methyl, ethyl, n-propyl, isopropyl, n-butyl, sec-butyl, isobutyl or tert-butyl.

$C_1$-$C_3$-Alkoxy is in the context of the present invention a linear or branched alkyl radical linked via an oxygen atom and having 1 to 3 carbon atoms. Examples are methoxy, ethoxy, n-propoxy and isopropoxy.

The compounds of the invention of the formula I, their pharmacologically acceptable salts and their prodrugs may also be present in the form of solvates or hydrates. Solvates mean in the context of the present invention crystalline forms of the compounds I or of their pharmaceutically acceptable salts or prodrugs thereof which comprise solvent molecules incorporated in the crystal lattice. The solvent molecules are preferably incorporated in stoichiometric ratios. Hydrates are a specific form of solvates; the solvent in this case is water.

The statements made hereinafter concerning suitable and preferred features of the invention, especially concerning the radicals $R^1$, $R^2$, $R^3$, $X^1$ and $X^2$ in the compound I, but also concerning the features of the process of the invention and of the use according to the invention apply both taken on their own and preferably in any possible combination with one another.

The compounds I are preferably provided in the form of the free base (i.e. according to structural formula I) or in the form of their acid addition salts.

In a preferred embodiment, $R^1$ is hydrogen or methoxy.

In a further preferred embodiment, $R^3$ is hydrogen, methyl or ethyl.

In a further preferred embodiment, one of the variables $X^1$, $X^2$ is N and the other is CH.

In a particularly preferred embodiment in this connection, $X^1$ is N and $X^2$ is CH.

In an alternatively particularly preferred embodiment, $X^1$ is CH and $X^2$ is N.

The invention preferably relates to compounds of the formula I in which
$R^1$ is hydrogen or methoxy;
$R^2$ is hydrogen or methoxy;
$R^3$ is hydrogen, methyl, ethyl, n-propyl or isopropyl, preferably hydrogen, methyl or ethyl;
$X^1$ is N or CH;
$X^2$ is N or CH;
where $X^1$ and $X^2$ are not simultaneously N;
and the pharmaceutically acceptable salts and prodrugs thereof. In a particular embodiment, the variables $X^1$ and $X^2$ are not simultaneously CH, i.e. preferably one of the variables $X^1$ or $X^2$ is N and the other is CH.

The invention particularly preferably relates to compounds of the formula I in which
$R^1$ is hydrogen or methoxy;
$R^2$ is hydrogen or methoxy;
$R^3$ is hydrogen, methyl or ethyl;
$X^1$ is N;
$X^2$ is CH;
and the pharmaceutically acceptable salts and prodrugs thereof.

Among these, preference is given to the compound I in which
$R^1$ is methoxy;
$R^2$ is methoxy;

$R^3$ is methyl;
$X^1$ is N; and
$X^2$ is CH;
and the compound I in which
$R^1$ is methoxy;
$R^2$ is methoxy;
$R^3$ is ethyl;
$X^1$ is N; and
$X^2$ is CH;
with more preference for the former compound.

The invention alternatively particularly preferably relates to compounds of the formula I in which
$R^1$ is hydrogen or methoxy;
$R^2$ is hydrogen or methoxy;
$R^3$ is hydrogen, methyl or ethyl;
$X^1$ is CH;
$X^2$ is N;
and the pharmaceutically acceptable salts and prodrugs thereof.

Among these, preference is given to the compound I in which
$R^1$ is methoxy;
$R^2$ is methoxy;
$R^3$ is methyl;
$X^1$ is CH; and
$X^2$ is N;
and the compound I in which
$R^1$ is methoxy;
$R^2$ is methoxy;
$R^3$ is ethyl;
$X^1$ is CH; and
$X^2$ is N;
with more preference for the former compound.

The invention further particularly preferably relates to compounds of the formula I in which
$R^1$ is hydrogen or methoxy;
$R^2$ is hydrogen or methoxy;
$R^3$ is hydrogen, methyl or ethyl;
$X^1$ is CH;
$X^2$ is CH;
and the pharmaceutically acceptable salts and prodrugs thereof.

Among these, preference is given to the compound I in which
$R^1$ is methoxy;
$R^2$ is methoxy;
$R^3$ is methyl;
$X^1$ is CH; and
$X^2$ is CH;
and the compound I in which
$R^1$ is methoxy;
$R^2$ is methoxy;
$R^3$ is ethyl;
$X^1$ is CH; and
$X^2$ is CH;
with more preference for the former compound.

Examples of preferred embodiment of the present invention are compounds of the formula I and the pharmaceutically acceptable salts and prodrugs thereof, in which the radicals $X^1$, $X^2$, $R^1$, $R^2$ and $R^3$ assume in each case the meanings mentioned in each line in the following table 1.

TABLE 1

| Compound No. | $X^1$ | $X^2$ | $R^1$ | $R^2$ | $R^3$ |
|---|---|---|---|---|---|
| I-1 | N | CH | Methoxy | Methoxy | Methyl |
| I-2 | N | CH | Methoxy | H | Methyl |
| I-3 | N | CH | Ethoxy | H | Methyl |
| I-4 | N | CH | H | H | Methyl |
| I-5 | N | CH | H | Methoxy | Methyl |
| I-6 | N | CH | Ethoxy | Methoxy | Methyl |
| I-7 | N | CH | Methoxy | Methoxy | Ethyl |
| I-8 | N | CH | Methoxy | H | Ethyl |
| I-9 | N | CH | Ethoxy | H | Ethyl |
| I-10 | N | CH | H | H | Ethyl |
| I-11 | N | CH | H | Methoxy | Ethyl |
| I-12 | N | CH | Ethoxy | Methoxy | Ethyl |
| I-13 | N | CH | Methoxy | Methoxy | n-Propyl |
| I-14 | N | CH | Methoxy | H | n-Propyl |
| I-15 | N | CH | Ethoxy | H | n-Propyl |
| I-16 | N | CH | H | H | n-Propyl |
| I-17 | N | CH | H | Methoxy | n-Propyl |
| I-18 | N | CH | Ethoxy | Methoxy | n-Propyl |
| I-19 | N | CH | Methoxy | Methoxy | Isopropyl |
| I-20 | N | CH | Methoxy | H | Isopropyl |
| I-21 | N | CH | Ethoxy | H | Isopropyl |
| I-22 | N | CH | H | H | Isopropyl |
| I-23 | N | CH | H | Methoxy | Isopropyl |
| I-24 | N | CH | Ethoxy | Methoxy | Isopropyl |
| I-25 | N | CH | Methoxy | Methoxy | H |
| I-26 | N | CH | Methoxy | H | H |
| I-27 | N | CH | Ethoxy | H | H |
| I-28 | N | CH | H | H | H |
| I-29 | N | CH | H | Methoxy | H |
| I-30 | N | CH | Ethoxy | Methoxy | H |
| I-31 | CH | N | Methoxy | Methoxy | Methyl |
| I-32 | CH | N | Methoxy | H | Methyl |
| I-33 | CH | N | Ethoxy | H | Methyl |
| I-34 | CH | N | H | H | Methyl |
| I-35 | CH | N | H | Methoxy | Methyl |
| I-36 | CH | N | Ethoxy | Methoxy | Methyl |
| I-37 | CH | N | Methoxy | Methoxy | Ethyl |
| I-38 | CH | N | Methoxy | H | Ethyl |
| I-39 | CH | N | Ethoxy | H | Ethyl |
| I-40 | CH | N | H | H | Ethyl |
| I-41 | CH | N | H | Methoxy | Ethyl |
| I-42 | CH | N | Ethoxy | Methoxy | Ethyl |
| I-43 | CH | N | Methoxy | Methoxy | n-Propyl |
| I-44 | CH | N | Methoxy | H | n-Propyl |
| I-45 | CH | N | Ethoxy | H | n-Propyl |
| I-46 | CH | N | H | H | n-Propyl |
| I-47 | CH | N | H | Methoxy | n-Propyl |
| I-48 | CH | N | Ethoxy | Methoxy | n-Propyl |
| I-49 | CH | N | Methoxy | Methoxy | Isopropyl |
| I-50 | CH | N | Methoxy | H | Isopropyl |
| I-51 | CH | N | Ethoxy | H | Isopropyl |
| I-52 | CH | N | H | H | Isopropyl |
| I-53 | CH | N | H | Methoxy | Isopropyl |
| I-54 | CH | N | Ethoxy | Methoxy | Isopropyl |
| I-55 | CH | N | Methoxy | Methoxy | H |
| I-56 | CH | N | Methoxy | H | H |
| I-57 | CH | N | Ethoxy | H | H |
| I-58 | CH | N | H | H | H |
| I-59 | CH | N | H | Methoxy | H |
| I-60 | CH | N | Ethoxy | Methoxy | H |
| I-61 | CH | CH | Methoxy | Methoxy | Methyl |
| I-62 | CH | CH | Methoxy | H | Methyl |
| I-63 | CH | CH | Ethoxy | H | Methyl |
| I-64 | CH | CH | H | H | Methyl |
| I-65 | CH | CH | H | Methoxy | Methyl |
| I-66 | CH | CH | Ethoxy | Methoxy | Methyl |
| I-67 | CH | CH | Methoxy | Methoxy | Ethyl |
| I-68 | CH | CH | Methoxy | H | Ethyl |
| I-69 | CH | CH | Ethoxy | H | Ethyl |
| I-70 | CH | CH | H | H | Ethyl |
| I-71 | CH | CH | H | Methoxy | Ethyl |
| I-72 | CH | CH | Ethoxy | Methoxy | Ethyl |
| I-73 | CH | CH | Methoxy | Methoxy | n-Propyl |
| I-74 | CH | CH | Methoxy | H | n-Propyl |
| I-75 | CH | CH | Ethoxy | H | n-Propyl |
| I-76 | CH | CH | H | H | n-Propyl |
| I-77 | CH | CH | H | Methoxy | n-Propyl |

TABLE 1-continued

| Compound No. | $X^1$ | $X^2$ | $R^1$ | $R^2$ | $R^3$ |
|---|---|---|---|---|---|
| I-78 | CH | CH | Ethoxy | Methoxy | n-Propyl |
| I-79 | CH | CH | Methoxy | Methoxy | Isopropyl |
| I-80 | CH | CH | Methoxy | H | Isopropyl |
| I-81 | CH | CH | Ethoxy | H | Isopropyl |
| I-82 | CH | CH | H | H | Isopropyl |
| I-83 | CH | CH | H | Methoxy | Isopropyl |
| I-84 | CH | CH | Ethoxy | Methoxy | Isopropyl |
| I-85 | CH | CH | Methoxy | Methoxy | H |
| I-86 | CH | CH | Methoxy | H | H |
| I-87 | CH | CH | Ethoxy | H | H |
| I-88 | CH | CH | H | H | H |
| I-89 | CH | CH | H | Methoxy | H |
| I-90 | CH | CH | Ethoxy | Methoxy | H |

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i.e. minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts and the prodrugs of the pure enantiomers of compounds I, and the mixtures of enantiomers in the form of the pharmaceutically acceptable salts and prodrugs of compounds I.

Preferred embodiments of the invention are compounds of the formula I as detailed above which are characterized in that they are in optically active form, and the enantiomer of the relevant compound of the formula I is the one which rotates the plane of vibration of polarized light to the left (i.e. minus rotation), in the form of a free base, or a pharmaceutically acceptable salt or a prodrug thereof. The enantiomers with levorotation or minus rotation of the compounds I are also referred to hereinafter as (−) enantiomers.

Particular preference is given to compounds of the general formula I, pharmaceutically acceptable salts and their prodrugs as detailed above in which the corresponding (−) enantiomer is present in an optical purity (enantiomeric excess, ee) of more than 50% ee, particularly preferably of at least 80% ee, more preferably of at least 90% ee and even more preferably of at least 95% ee and in particular of at least 98% ee.

Likewise preferred embodiments of the invention are compounds of the general formula I as detailed above which are characterized in that they are in optically inactive form, i.e. in the form of the racemate, or in the form of a pharmaceutically acceptable salt or of a prodrug of the racemate.

The statements made in the context of the present invention concerning the direction of rotation of polarized light relate preferably to the signs [(+) or (−)] as determined in chloroform as solvent or in chloroform-containing solvent mixtures, in particular in chloroform.

Examples of particularly preferred compounds I are the compounds listed in following table 2 with the compound numbers I-1, I-1A, I-1B, I-2, I-2A, I-2B, I-4, I-4A, I-4B, I-5, I-5A, I-5B, I-7, I-7A, I-7B, I-8, I-8A, I-8B, I-10, I-10A, I-10B, I-11, I-11A, I-11B, I-31, I-31A, I-31B, I-32, I-32A, I-32B, I-34, I-34A, I-34B, I-35, I-35A, I-35B, I-37, I-37A, I-37B, I-38, I-38A, I-38B, I-40, I-40A, I-40B, I-41, I-41A, I-41B, I-61, I-61A and I-61B, and the pharmaceutically acceptable salts and prodrugs thereof. In this connection, the examples which are only designated by numbers correspond to the racemate of the respective compounds, the examples with an appended letter "A" (1A, 2A, . . . ) correspond to the dextrorotatory (+) enantiomer and the examples with an appended letter "B" (1B, 2B, . . . ) correspond to the levorotatory (−) enantiomer of the respective compound 1, 2, . . . .

TABLE 2

| Compound No. | $X^1$ | $X^2$ | $R^1$ | $R^2$ | $R^3$ | IUPAC Name |
|---|---|---|---|---|---|---|
| I-1 | N | CH | Methoxy | Methoxy | Methyl | (±)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile |
| I-1A | N | CH | Methoxy | Methoxy | Methyl | (+)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile |
| I-1B | N | CH | Methoxy | Methoxy | Methyl | (−)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile |
| I-2 | N | CH | Methoxy | H | Methyl | (±)-3-(2-Ethoxypyridin-3-yl)-1-(2-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |
| I-2A | N | CH | Methoxy | H | Methyl | (+)-3-(2-Ethoxypyridin-3-yl)-1-(2-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |

TABLE 2-continued

| Compound No. | X¹ | X² | R¹ | R² | R³ | IUPAC Name |
|---|---|---|---|---|---|---|
| I-2B | N | CH | Methoxy | H | Methyl | (−)-3-(2-Ethoxypyridin-3-yl)-1-(2-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |
| I-4 | N | CH | H | H | Methyl | (±)-1-Phenylsulfonyl-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile |
| I-4A | N | CH | H | H | Methyl | (+)-1-Phenylsulfonyl-3-(2-ethoxypyridin-3-yl)-3-{2-[4-(1-methylpiperidin-4-yl)-piperazin-1-yl]-2-oxoethyl}-2-oxo-2,3-dihydro-1H-indole-5-carbonitrile |
| I-4B | N | CH | H | H | Methyl | (−)-1-Phenylsulfonyl-3-(2-ethoxypyridin-3-yl)-3-{2-[4-(1-methylpiperidin-4-yl)-piperazin-1-yl]-2-oxoethyl}-2-oxo-2,3-dihydro-1H-indole-5-carbonitrile |
| I-5 | N | CH | H | Methoxy | Methyl | (±)-3-(2-Ethoxypyridin-3-yl)-1-(4-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |
| I-5A | N | CH | H | Methoxy | Methyl | (+)-3-(2-Ethoxypyridin-3-yl)-1-(4-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |
| I-5B | N | CH | H | Methoxy | Methyl | (−)-3-(2-Ethoxypyridin-3-yl)-1-(4-methoxyphenylsulfonyl)-3-{2-[4-(1-methyl-piperidin-4-yl)piperazin-1-yl]-2-oxoethyl}-2-oxo-2,3-dihydro-1H-indole-5-carbonitrile |
| I-7 | N | CH | Methoxy | Methoxy | Ethyl | (±)-1-(2,4-Dimethoxyphenylsulfonyl)-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile |
| I-7A | N | CH | Methoxy | Methoxy | Ethyl | (+)-1-(2,4-Dimethoxyphenylsulfonyl)-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile |
| I-7B | N | CH | Methoxy | Methoxy | Ethyl | (−)-1-(2,4-Dimethoxyphenylsulfonyl)-3-(2-ethoxypyridin-3-yl)-3-{2-[4-(1-ethyl-piperidin-4-yl)piperazin-1-yl]-2-oxoethyl}-2-oxo-2,3-dihydro-1H-indole-5-carbonitrile |
| I-8 | N | CH | Methoxy | H | Ethyl | (±)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile |
| I-8A | N | CH | Methoxy | H | Ethyl | (+)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile |
| I-8B | N | CH | Methoxy | H | Ethyl | (−)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile |
| I-10 | N | CH | H | H | Ethyl | (±)-1-Phenylsulfonyl-3-(2-ethoxypyridin-3-yl)-3-{2-[4-(1-ethylpiperidin-4-yl)-piperazin-1-yl]-2-oxoethyl}-2-oxo-2,3-dihydro-1H-indole-5-carbonitrile |
| I-10A | N | CH | H | H | Ethyl | (+)-1-Phenylsulfonyl-3-(2-ethoxypyridin-3-yl)-3-{2-[4-(1-ethylpiperidin-4-yl)-piperazin-1-yl]-2-oxoethyl}-2-oxo-2,3-dihydro-1H-indole-5-carbonitrile |
| I-10B | N | CH | H | H | Ethyl | (−)-1-Phenylsulfonyl-3-(2-ethoxypyridin-3-yl)-3-{2-[4-(1-ethylpiperidin-4-yl)-piperazin-1-yl]-2-oxoethyl}-2-oxo-2,3-dihydro-1H-indole-5-carbonitrile |
| I-11 | N | CH | H | Methoxy | Ethyl | (±)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile |
| I-11A | N | CH | H | Methoxy | Ethyl | (+)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile |
| I-11B | N | CH | H | Methoxy | Ethyl | (−)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile |
| I-31 | CH | N | Methoxy | Methoxy | Methyl | (±)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |
| I-31A | CH | N | Methoxy | Methoxy | Methyl | (+)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |
| I-31B | CH | N | Methoxy | Methoxy | Methyl | (−)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |
| I-32 | CH | N | Methoxy | H | Methyl | (±)-3-(2-Ethoxypyridin-3-yl)-1-(2-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-32A | CH | N | Methoxy | H | Methyl | (+)-3-(2-Ethoxypyridin-3-yl)-1-(2-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-32B | CH | N | Methoxy | H | Methyl | (−)-3-(2-Ethoxypyridin-3-yl)-1-(2-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-34 | CH | N | H | H | Methyl | (±)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |
| I-34A | CH | N | H | H | Methyl | (+)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |
| I-34B | CH | N | H | H | Methyl | (−)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile |

TABLE 2-continued

| Compound No. | X¹ | X² | R¹ | R² | R³ | IUPAC Name |
|---|---|---|---|---|---|---|
| I-35 | CH | N | H | Methoxy | Methyl | (±)-3-(2-Ethoxypyridin-3-yl)-1-(4-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-35A | CH | N | H | Methoxy | Methyl | (+)-3-(2-Ethoxypyridin-3-yl)-1-(4-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-35B | CH | N | H | Methoxy | Methyl | (−)-3-(2-Ethoxypyridin-3-yl)-1-(4-methoxyphenylsulfonyl)-3-{2-[4-(4-methyl-piperazin-1-yl)piperidin-1-yl]-2-oxoethyl}-2-oxo-2,3-dihydro-1H-indole-5-carbonitrile |
| I-37 | CH | N | Methoxy | Methoxy | Ethyl | (±)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile |
| I-37A | CH | N | Methoxy | Methoxy | Ethyl | (+)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile |
| I-37B | CH | N | Methoxy | Methoxy | Ethyl | (−)-1-(2,4-Dimethoxyphenylsulfonyl)-3-(2-ethoxypyridin-3-yl)-3-{2-[4-(4-ethyl-piperazin-1-yl)piperidin-1-yl]-2-oxoethyl}-2-oxo-2,3-dihydro-1H-indole-5-carbonitrile |
| I-38 | CH | N | Methoxy | H | Ethyl | (±)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile |
| I-38A | CH | N | Methoxy | H | Ethyl | (+)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile |
| I-38B | CH | N | Methoxy | H | Ethyl | (−)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile |
| I-40 | CH | N | H | H | Ethyl | (±)-1-Phenylsulfonyl-3-(2-ethoxypyridin-3-yl)-3-{2-[4-(4-ethylpiperazin-1-yl)-piperidin-1-yl]-2-oxoethyl}-2-oxo-2,3-dihydro-1H-indole-5-carbonitrile |
| I-40A | CH | N | H | H | Ethyl | (+)-1-Phenylsulfonyl-3-(2-ethoxypyridin-3-yl)-3-{2-[4-(4-ethylpiperazin-1-yl)-piperidin-1-yl]-2-oxoethyl}-2-oxo-2,3-dihydro-1H-indole-5-carbonitrile |
| I-40B | CH | N | H | H | Ethyl | (−)-1-Phenylsulfonyl-3-(2-ethoxypyridin-3-yl)-3-{2-[4-(4-ethylpiperazin-1-yl)-piperidin-1-yl]-2-oxoethyl}-2-oxo-2,3-dihydro-1H-indole-5-carbonitrile |
| I-41 | CH | N | H | Methoxy | Ethyl | (±)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile |
| I-41A | CH | N | H | Methoxy | Ethyl | (+)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile |
| I-41B | CH | N | H | Methoxy | Ethyl | (−)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile |
| I-61 | CH | CH | Methoxy | Methoxy | Methyl | (±)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile |
| I-61A | CH | CH | Methoxy | Methoxy | Methyl | (+)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile |
| I-61B | CH | CH | Methoxy | Methoxy | Methyl | (−)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile |

Among these, particular preference is given to the racemates (i.e. compounds 1, 2, . . . ) and their physiologically tolerated salts and prodrugs thereof. Also particularly preferred are the (−) enantiomers (i.e. compounds 1B, 2B, . . . ) and their physiologically tolerated salt and prodrugs thereof. The aforementioned compounds are provided in particular in the form of their free base or in the form of their acid addition salts.

Examples of synthetic routes for preparing the oxindole derivatives of the invention are described below.

The oxindoles of the invention can be prepared in various ways, and the preparation is outlined in the synthesis scheme. The variables in this synthesis scheme have the same meanings as in formula I.

The 3-hydroxy-1,3-dihydroindol-2-ones IV can be obtained by addition of metallated heterocycles III onto the 3-keto group of the isatins II. The metallated heterocycles, such as, for example, the corresponding Grignard (Mg) or organyllithium compound, can be obtained in any conventional way from halogen or hydrocarbon compounds. Examples of methods are present in Houben-Weyl, Methoden der Organischen Chemie, vol. 13, 1-2, chapter on Mg and Li compounds, and in WO 2005/030755 and WO 2006/2006005609. The isatins II are either commercially available or can be prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV which contain for example in position 5 an iodine as radical $R^a$ in the 6-membered aromatic can be converted with KCN or $Zn(CN)_2$ with Pd(0) catalysis in solvents such as dimethylformamide or tetrahydrofuran and, where appropriate also with the addition of bases such as $K_2CO_3$ or other carbonates or amines, at elevated temperature into the analogous cyan-containing 3-hydroxyoxindole IV. It is possible to take as Pd(0) salts for example transition metal complexes prepared in situ from $PdCl_2$ or $PdOAc_2$ by adding phosphines such as tris(ortho-tolyl)phosphine. Commercial palladium complexes such as, for example, the catalyst tetrakis(triphenylphosphine)palladium(0) and/or additions of phosphine ligands can likewise be employed. Examples of the cyanation of 5-iodo-substituted oxindoles are to be found in WO 2005/030755 and WO 2006/005609.

The 3-hydroxyoxindoles IV can be converted into the compounds V which have a leaving group LG in position 3, where the leaving group LG can be a conventional leaving group such as, for example, halide, mesylate or tosylate. The intermediate V with for example LG=chlorine can be prepared by treating the alcohol IV with thionyl chloride in the presence of a base such as, for example, pyridine.

Introduction of the acetic acid group can take place as described in WO 2006/005609 in a 4-stage sequence (1. replacement of the leaving group LG in IV by the sodium salt of dimethyl malonate, 2. hydrolysis of the first ester group, 3. thermal decarboxylation, 4. hydrolysis of the second ester group).

The amine side chain X can be coupled to the carboxylic acid VIII using standard coupling reagents known in peptide chemistry, such as, for example, EDC (N-(3-dimethylaminopropyl)-N'-ethylcarbodiimide hydrochloride) and HOBT (1-hydroxybenzo-triazole) in a solvent such as, for example, N,N-dimethylformamide. The amines X can be either purchased or prepared by methods known from the literature. Compounds of the invention with $R^3$=H can be prepared by using appropriate Boc-protected amines X ($R^3$=Boc). The Boc protective group can be removed after sulfonylation, for example by treatment with trifluoroacetic acid in dichloromethane.

The sulfonylation can take place by deprotonation of the coupling product IX with a strong base such as, for example, sodium hydride or potassium tert-butoxide, and subsequent treatment with sulfonyl chlorides XI in a solvent such as, for example, DMF, and leads to the compounds I of the invention. The sulfonyl chlorides XI employed can either be purchased or be prepared in analogy to known processes (see for example J. Med. Chem. 40, 1149 (1997)).

SYNTHESIS SCHEME

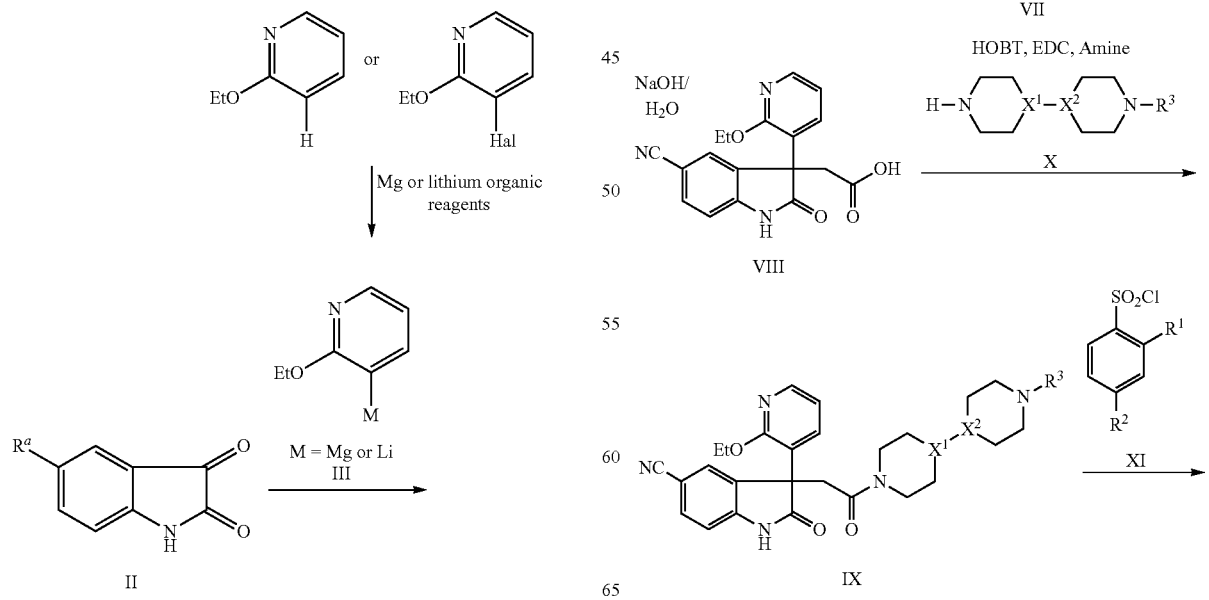
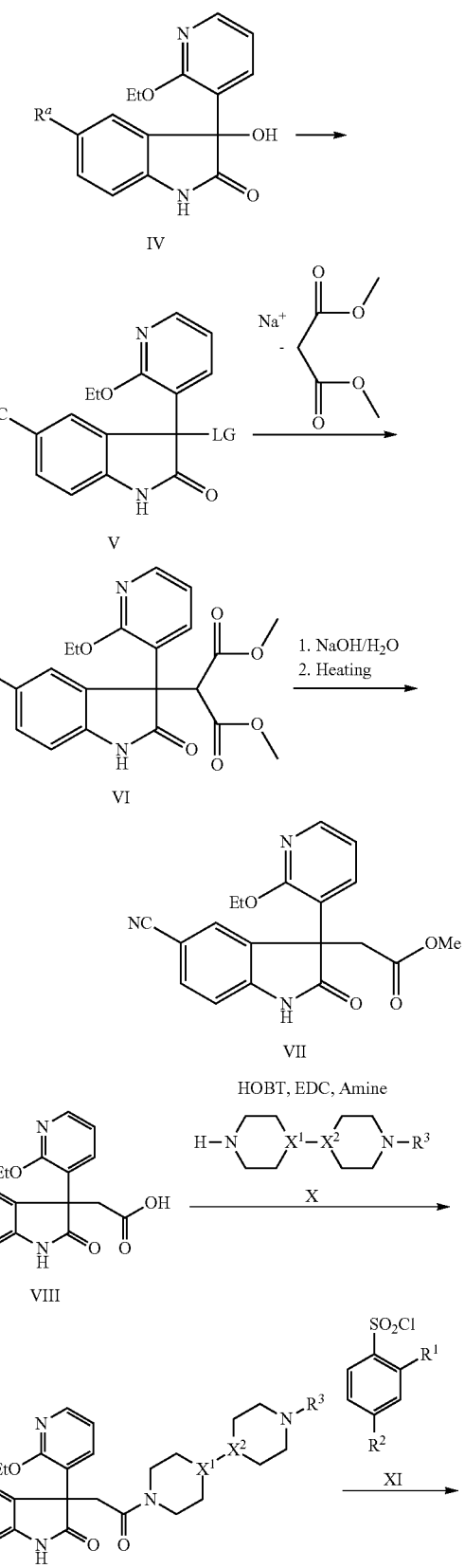

-continued

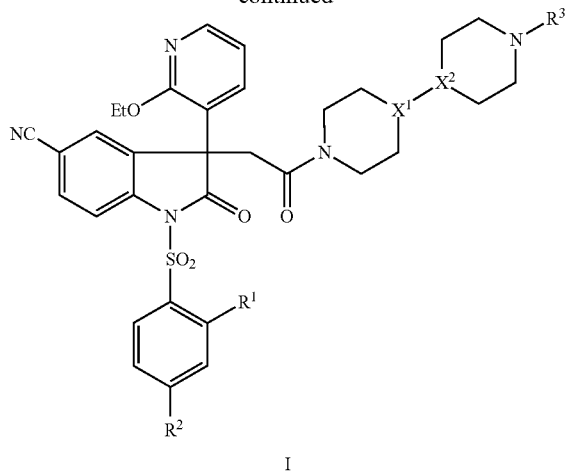

EtO = Ethoxy
R$^a$ = CN or iodine

A further preparation possibility for compounds of the invention with R$^3$=methyl, ethyl, n-propyl or isopropyl is reaction of the secondary piperidine or piperazine compounds I (R$^3$=H) with aldehydes or ketones in the presence of reducing agents such as, for example, sodium cyanoborohydride or sodium acetoxyborohydride in the manner of a reductive amination (J. March, Advanced Organic Chemistry, 1992, 4th edition, Wiley, New York, pages 411; 898).

A further aspect of the present invention relates to a pharmaceutical composition comprising at least one compound of the general formula I and/or a pharmaceutically acceptable salt or a prodrug thereof as detailed above, and a pharmaceutically acceptable carrier. Suitable carriers depend inter alia on the dosage form of the composition and are known in principle to the skilled worker. Some suitable carriers are described hereinafter.

A further aspect of the present invention relates to the use of compounds of the formula I and/or of pharmaceutically acceptable salts or prodrugs thereof for the manufacture of a medicament for the treatment and/or prophylaxis of vasopressin-dependent diseases.

Vasopressin-dependent diseases are those in which the progress of the disease is at least partly dependent on vasopressin, i.e. diseases which show an elevated vasopressin level which may contribute directly or indirectly to the pathological condition. In other words, vasopressin-dependent diseases are those which can be influenced by modulating the vasopressin receptor, for example by administration of a vasopressin receptor ligand (agonist, antagonist, partial antagonist/agonist, inverse agonist etc.).

In a preferred embodiment, the present invention relates to the use of compounds of the invention of the formula I or of pharmaceutically acceptable salts or prodrugs for the manufacture of a medicament for the treatment and/or prophylaxis of diseases selected from diabetes, insulin resistance, nocturnal enuresis, incontinence and diseases in which impairments of blood clotting occur, and/or for delaying micturition. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of pharmaceutically acceptable salts or prodrugs thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness.

The compounds of the invention of the formula I or their pharmaceutically acceptable salts or prodrugs or the pharmaceutical composition of the invention can also be used for the treatment of various vasopressin-dependent complaints which have central nervous causes or alterations in the HPA axis (hypothalamic pituitary adrenal axis), for example for affective disorders such as depressive disorders and bipolar disorders. These include for example dysthymic disorders, phobias, post-traumatic stress disorders, general anxiety disorders, panic disorders, seasonal depression and sleep disorders.

The compounds of the invention of the formula I and their pharmaceutically acceptable salts or prodrugs or the pharmaceutical composition of the invention can likewise be employed for the treatment of anxiety disorders and stress-dependent anxiety disorders, such as, for example, generalized anxiety disorders, phobias, post-traumatic anxiety disorders, panic anxiety disorders, obsessive-compulsive anxiety disorders, acute stress-dependent anxiety disorders and social phobia.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of pharmaceutically acceptable salts or prodrugs thereof for the manufacture of a medicament for the treatment of affective disorders.

In a further preferred embodiment, the present invention relates to the use of compounds of the invention of the formula I or of pharmaceutically acceptable salts or prodrugs thereof for the manufacture of a medicament for the treatment of anxiety disorders and/or stress-dependent anxiety disorders.

In a further preferred embodiment, the present invention relates to the use of compounds of the invention of the formula I or of pharmaceutically acceptable salts or prodrugs thereof for the manufacture of a medicament for the treatment of memory impairments and/or Alzheimer's disease.

In a further preferred embodiment, the present invention relates to the use of compounds of the invention of the formula I or of pharmaceutically acceptable salts or prodrugs thereof for the manufacture of a medicament for the treatment of psychoses and/or psychotic disorders.

In a further preferred embodiment, the present invention relates to the use of compounds of the invention of the formula I or of pharmaceutically acceptable salts or prodrugs thereof for the manufacture of a medicament for the treatment of Cushing's syndrome or other stress-dependent diseases.

In a further preferred embodiment, the present invention relates to the use of compounds of the invention of the formula I or of pharmaceutically acceptable salts or prodrugs thereof for the manufacture of a medicament for the treatment of sleep disorders.

In a further preferred embodiment, the present invention relates to the use of compounds of the invention of the formula I or of pharmaceutically acceptable salts or prodrugs thereof for the manufacture of a medicament for the treatment of depressive disorders. A particular form of depressive disorders are so-called childhood onset mood disorders, i.e. depressive moods having their onset in childhood.

In a further preferred embodiment, the present invention relates to the use of compounds of the invention of the formula I or of pharmaceutically acceptable salts or prodrugs thereof for the manufacture of a medicament for the treatment of vasomotor symptoms and/or thermoregulatory dysfunctions such as, for example, the hot flush symptom.

In a further preferred embodiment, the present invention relates to the use of compounds of the invention of the formula I or of pharmaceutically acceptable salts or prodrugs thereof for the manufacture of a medicament for the treatment and/or prophylaxis of drug or pharmaceutical dependencies and/or dependencies mediated by other factors, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors.

In a further preferred embodiment, the present invention relates to the use of compounds of the invention of the formula I or of pharmaceutically acceptable salts or prodrugs thereof for the manufacture of a medicament for the treatment and/or prophylaxis of schizophrenia and/or psychosis.

A further aspect of the invention relates to a method for the treatment and/or prophylaxis of vasopressin-dependent diseases, in which an effective amount of at least one compound of the invention of the formula I or of at least one pharmaceutically acceptable salt or one prodrug thereof or of a pharmaceutical composition of the invention is administered to a patient.

Concerning the definition of vasopressin-dependent diseases, reference is made to the above statements.

In a preferred embodiment of the invention, the method of the invention serves for the treatment and/or prophylaxis of disorders selected from diabetes, insulin resistance, nocturnal enuresis, incontinence and diseases in which impairments of blood clotting occur, and/or for delaying micturition. Concerning the definition of diabetes, reference is made to the above statements.

In a further preferred embodiment, the method of the invention serves for the treatment and/or prophylaxis of disorders selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastric vasospasm, hepatocirrhosis, gastric and intestinal ulcers, emesis, emesis occurring during chemotherapy, and travel sickness.

In a further preferred embodiment, the method of the invention serves for the treatment and/or prophylaxis of affective disorders.

In a further preferred embodiment, the method of the invention serves for the treatment and/or prophylaxis of anxiety disorders and/or stress-dependent anxiety disorders.

In a further preferred embodiment, the method of the invention serves for the treatment and/or prophylaxis of memory impairments and/or Alzheimer's disease.

In a further preferred embodiment, the method of the invention serves for the treatment and/or prophylaxis of psychoses and/or psychotic disorders.

In a further preferred embodiment, the method of the invention serves for the treatment and/or prophylaxis of Cushing's syndrome.

In a further preferred embodiment, the method of the invention serves for the treatment and/or prophylaxis of sleep disorders in a patient.

In a further preferred embodiment, the method of the invention serves for the treatment and/or prophylaxis of depressive disorders. In the case of depressive disorders, specific mention is also to be made of childhood onset mood disorders, i.e. depressive moods having their onset in childhood.

In a further preferred embodiment, the method of the invention serves for the treatment and/or prophylaxis of vasomotor symptoms and/or thermoregulatory dysfunctions, such as, for example, the hot flush symptom.

In a further preferred embodiment, the method of the invention serves for the treatment and/or prophylaxis of drug or pharmaceutical dependencies and/or dependencies mediated by other factors, for the treatment and/or prophylaxis of stress caused by withdrawal of one or more factors mediating the dependence, and/or for the treatment and/or prophylaxis of stress-induced relapses into drug or pharmaceutical dependencies and/or dependencies mediated by other factors.

In a further preferred embodiment, the method of the invention serves for the treatment and/or prophylaxis of schizophrenia and/or psychosis.

The patient to be treated prophylactically or therapeutically with the method of the invention is preferably a mammal, for example a human or a nonhuman mammal or a nonhuman transgenic mammal. Specifically it is a human.

The compounds of the general formula I, their pharmaceutically acceptable salts and prodrugs as detailed above can be prepared by a skilled worker with knowledge of the technical teaching of the invention in implementing and/or in analogous implementation of process steps known per se.

The compounds I or their prodrugs and/or their pharmaceutically acceptable salts are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I or their prodrugs and/or their pharmaceutically acceptable salts are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-dependent diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention, of a pharmaceutically acceptable salt or of a prodrug thereof and suitable pharmaceutical carriers (drug carriers).

These drug carriers are chosen according to the pharmaceutical form and the desired mode of administration and are known in principle to the skilled worker.

The compounds of the invention of the formula I or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, salt or a prodrug thereof.

The invention is explained in more detail below by means of examples, but the examples are not to be understood to be restrictive.

The compounds of the invention can be prepared by various synthetic routes. The methods mentioned, as described accordingly in the synthesis scheme, are explained in greater detail merely by way of example using the given examples without being exclusively restricted to the synthesis routes or analogous methods.

EXPERIMENTAL SECTION

Abbreviations Used

THF: tetrahydrofuran
DMSO: dimethyl sulfoxide
TFA: trifluoroacetic acid
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets I. Preparation of the Starting Compound X a) 1-Ethyl-4-piperidin-4-yl-piperazine a.1 tert-Butyl 4-(4-ethylpiperazin-1-yl)piperidine-1-carboxylate 29.2 g (256 mmol) of N-ethylpiperazine were introduced with 50.0 g (256 mmol) of tert-butyl 4-oxopiperidine-1-carboxylate (corresponds to 1-Boc-4-piperidone) into 800 ml of ethanol while cooling in ice. 15.4 g (256 mmol) of glacial acetic acid were added. Then 16.1 g (256 mmol) of sodium acetoxyborohydride were added in portions to the cooled reaction mixture. Initially slight gas formation was observed and, after addition of ⅔ of the reducing agent, foam formation was observed. The reaction mixture was stirred at room temperature overnight. The reaction solution was worked up by adding 200 ml of 2N of sodium hydroxide solution while cooling, distilling out the solvent ethanol and diluting the remaining reaction mixture with water. It was extracted with diethyl ether (2×) and was washed with saturated sodium chloride solution (1×), and the combined organic phases were dried over magnesium sulfate and filtered, and the solvent was removed in vacuo. The crude title compound was obtained as a yellow oil which was then chromatographed on a 4 l suction funnel filled with silica gel using dichloromethane and 10% methanol as eluent. In total, 40 g (135 mmol, 53%) of tert-butyl 4-(4-ethylpiperazin-1-yl)piperidine-1-carboxylate were obtained.

a.2 1-Ethyl-4-piperidin-4-ylpiperazine as Chloride Salt

The protective group was removed by introducing 40 g (135 mmol) of tert-butyl 4-(4-ethylpiperazin-1-yl)piperidine-1-carboxylate from example a.1 into 200 ml of methanol and 1.8 l of dichloromethane and adding 100 ml of 5-6M HCl solution in isopropanol. A suspension resulted, and slight gas evolution was also observable. The reaction mixture was stirred at 40° C. (water bath temperature) for one hour and then stirred at room temperature for 48 hours. For complete deprotection, 50 ml of the 5-6M HCl solution in isopropanol were again added and the reaction mixture was stirred at 40° C. The dichloromethane was distilled out in a rotary evaporator. 200 ml of methanol and 30 ml of the 5-6M HCl solution in isopropanol were again added. The reaction mixture was stirred under reflux for one hour, during which a white suspension formed with strong evolution of gas. A mobile suspension then resulted and was cooled to room temperature. The precipitate was filtered off with suction and washed with methanol and diethyl ether. After drying, 36 g (117 mmol, 87%) of 1-ethyl-4-piperidin-4-ylpiperazine were isolated as chloride salt.

$^1$H-NMR (D$_2$O, 400 MHz) δ[ppm]=3.74-3.47 (m, 11H), 3.28 (q, 2H, J=7.3 Hz), 3.06 (dt, 2H, J=2.2 Hz, J=13.2 Hz), 2.38 (m, 2H, J=13.6 Hz), 1.89 (dq, 2H, J=4.1 Hz, J=13.3 Hz), 1.30 (t, 3H, J=7.3 Hz).

II. Preparation of the Racemic Compounds of the Formula I

Example 1

(±)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile, Trifluoroacetic Acid Salt (compound I-34)

1.1 3-(2-Ethoxypyridin-3-yl)-3-hydroxy-5-iodo-1,3-dihydro-2H-indol-2-one 3.22 g (80.50 mmol, 60% w/w) of sodium hydride were added in portions to 20.86 g (76.40 mmol) of 5-iodoisatin in 400 ml of anhydrous tetrahydrofuran (THF) while stirring and cooling in an ice bath to keep the temperature at between 0-10° C. The suspension was stirred while cooling in an ice bath for one hour.

To prepare the pyridine Grignard 20 g (80.30 mmol) of 2-ethoxy-3-iodopyridine were dissolved in 400 ml of anhydrous THF at room temperature. 95.6 ml (1M solution in THF, 95.60 mmol) of ethylmagnesium bromide were added to this solution while cooling at a temperature between 22 and 15° C. within 5-10 minutes. The solution was stirred for 20 minutes, during which it became a pale yellowish color from colorless.

The solution of the pyridine Grignard was then added to the solution, cooled in an ice bath, of the 5-iodoisatin sodium salt at a temperature between 5 and 18° C. within 5-10 minutes. After addition of the pyridine Grignard was complete, the ice bath was removed. The reaction mixture was stirred at room temperature for 2 hours. An excess of saturated ammonium chloride solution was added, followed by ethyl acetate. The mixture was stirred for a further 5 minutes. The aqueous phase was separated off and extracted with ethyl acetate (2×). The combined organic phases were washed with water (2×), and the solvent was removed in vacuo. During this, unreacted 5-iodoisatin precipitated first from the still dilute solution and was separated off. After further concentration, finally the title compound also crystallized. The suspension was stored in a refrigerator at 5° C. for 2 hours. The precipitated, pale yellow solid was then filtered off and washed with a little ethyl acetate. After drying at 40° C., the title compound (17.1 g, 43.16 mmol, 57%) was obtained.

ESI-MS [M+H$^+$]=397 calculated for C$_{15}$H$_{13}$IN$_2$O$_3$=396.19

1.2 5-Cyano-3-hydroxy-3-(2-ethoxypyridin-3-yl)-1,3-dihydroindol-2-one 7.1 g (17.92 mmol) of 3-(2-ethoxypyridin-3-yl)-3-hydroxy-5-iodo-1,3-dihydro-2H-indol-2-one were stirred in 100 ml of anhydrous THF under a nitrogen atmosphere at room temperature. 2.1 g (17.92 mmol) of zinc cyanide were added, followed by 0.51 g (0.45 mmol) of the catalyst tetrakis(triphenylphosphine)palladium(0). The reaction mixture was immediately placed in a preheated oil bath at a temperature of 100° C. The mixture was stirred at 100° C. (oil-bath temperature) and, after 30 minutes, a further 0.51 g (0.45 mmol) of the catalyst was added. The mixture was stirred for a total of 2 hours. The reaction mixture was allowed to cool to room temperature and an excess of water was added. It was subsequently extracted with ethyl acetate (3×), and the combined organic phases were washed three times with water. The solvent was evaporated to dryness in vacuo, and the residue was slurried with a small volume of ethyl acetate. A pale yellow solid was filtered off and was washed with ethyl acetate and dried in a vacuum drying oven. 3.7 g (12.44 mmol, 69.4%) of the title compound were obtained.

ESI-MS [M+H$^+$]=296 Calculated for C$_{16}$H$_{13}$N$_3$O$_3$=295.30

1.3 3-Chloro-3-(2-ethoxypyridin-3-yl)-2-oxoindoline-5-carbonitrile 2.30 ml (28.45 mmol) of pyridine were added to a suspension of 6.00 g (20.32 mmol) of 5-cyano-3-hydroxy-3-(2-ethoxypyridin-3-yl)-1,3-dihydroindol-2-one from example 1.2 in 60 ml of anhydrous dichloromethane (dried over molecular sieves) under nitrogen. After the reaction mixture had been cooled to 0° C., 2.06 ml (28.45 mmol) of thionyl chloride, undiluted, were added dropwise (exothermic reaction), and the reaction mixture was then stirred at room temperature for one hour. A yellow suspension formed. The progress of the reaction was followed by thin-layer chromatography (TLC) (silica gel, dichloromethane/methanol in the ratio 95:5). The reaction mixture was cautiously poured into ice-water. After stirring for 15 minutes, the organic phase was separated off. The aqueous phase was extracted with dichloromethane (2×). All the organic phases were combined and dried over magnesium sulfate and filtered, and the solvent was removed in vacuo. 5.70 g (18.17 mmol, 89%) of the title compound were obtained as an amorphous solid which was employed without further purification in the next stage.

1.4 Dimethyl[5-cyano-3-(2-ethoxypyridin-3-yl)-2-oxo-2,3-dihydro-1H-indol-3-yl]-malonate 5.68 ml (49.75 mmol) of dimethyl malonate were slowly added dropwise to a suspension, cooled to 10° C., of 1.808 g (45.23 mmol, 60% w/w) of sodium hydride in 100 ml of dimethylformamide. The reaction mixture was then stirred at room temperature for 30 minutes and subsequently 4.73 g (15.08 mmol) of 3-chloro-3-(2-ethoxypyridin-3-yl)-2-oxoindoline-5-carbonitrile from example 1.3 were added in portions undiluted. The reaction solution became dark red in color and was stirred at room temperature for a further 15 minutes. The progress of the reaction was checked by thin-layer chromatography (silica gel, heptane/ethyl acetate 1:1). The mixture was worked up by stirring into cold 1 N HCl and adding dichloromethane. The phases were separated, and the aqueous phase was extracted with dichloromethane (1×). The combined organic phase was washed firstly with water (1×) and then with saturated sodium chloride solution (1×), dried over magnesium sulfate and filtered, and the solvent was removed in vacuo. The residue was again partly dissolved in a little dichloromethane, and pentane was added. Several crystalline fractions were obtained. A total of 6.48 g (15.83 mmol, 100%) of the title compound was obtained as a yellow solid which was only slightly impure.

ESI-MS [M+H$^+$]=410 Calculated for $C_{21}H_{19}N_3O_6$=409.40

1.5 Methyl[5-cyano-3-(2-ethoxypyridin-3-yl)-2-oxo-2,3-dihydro-1H-indol-3-yl]acetate 60 ml of 2 N sodium hydroxide solution were added to a solution of 6.48 g (15.83 mmol) of dimethyl[5-cyano-3-(2-ethoxypyridin-3-yl)-2-oxo-2,3-dihydro-1H-indol-3-yl]malonate from example 1.4 in 6 ml of ethanol, and the mixture was stirred at room temperature for 1 hour. Precursor was then no longer detectable by a TLC check (silica gel, heptane/ethyl acetate 1:1). The reaction mixture was stirred into ice-cold 1 N hydrochloric acid, and dichloromethane was added. The phases were separated, and the aqueous phase was extracted once with dichloromethane. The combined organic phase was washed firstly with water (1×) and then with saturated sodium chloride solution (1×), dried over magnesium sulfate and filtered, and the solvent was removed in vacuo. The resulting yellowish solid (5.46 g) was dried in a vacuum drying oven at 40° C.

The resulting yellowish solid (5.46 g) was heated in a one-neck flask under a blanket of nitrogen to 150° C. During this, $CO_2$ gas was evolved and methyl[5-cyano-3-(2-ethoxypyridin-3-yl)-2-oxo-2,3-dihydro-1H-indol-3-yl]acetate formed. The reaction mixture was cooled to room temperature, and the substance was mixed with methanol. The crystals which formed were stored in a refrigerator at 5° C. overnight. The solid was filtered off with suction and washed with a little methanol. 2.2 g (5.95 mmol, 38%, 95% purity) of the title compound were obtained as a beige-colored solid.

ESI-MS [M+H$^+$]=352 Calculated for $C_{19}H_{17}N_3O_4$=351.37

1.6 [5-Cyano-3-(2-ethoxypyridin-3-yl)-2-oxo-2,3-dihydro-1H-indol-3-yl]acetic Acid Firstly 15 ml of water and then 9 ml of 2 N sodium hydroxide solution were added to a solution of 1.557 g (4.43 mmol) of methyl 5-cyano-3-(2-ethoxypyridin-3-yl)-2-oxo-2,3-dihydro-1H-indol-3-yl]acetate from example 1.5 in 6 ml of ethanol. The reaction mixture was stirred at room temperature for 5 hours. According to a TLC check (silica gel, dichloromethane/methanol 9:1), the reaction had proceeded to completion. For working up, the reaction mixture was adjusted to pH 5 with 1 N hydrochloric acid and then concentrated in a rotary evaporator. The residue was taken up in toluene and again concentrated to dryness. The resulting beige-colored solid was dried in a vacuum drying oven at 40° C. 2.70 g (4.43 mmol, 55% NaCl salt content, 99% of theory yield) of the title compound were obtained.

ESI-MS [M+H$^+$]=338 Calculated for $C_{18}H_{15}N_3O_4$=337.34

1.7 3-(2-Ethoxypyridin-3-yl)-3-{2-[4-(4-methylpiperazin-1-yl)piperidin-1-yl]-2-oxoethyl}-2-oxoindoline-5-carbonitrile 200 mg (1.48 mmol) of 1-hydroxybenzotriazole and 284 mg (1.48 mmol) of N-(3-dimethylaminopropyl)-N'-ethylcarbodiimide hydrochloride were added to a solution of 907 mg (1.48 mmol) of [5-cyano-3-(2-ethoxypyridin-3-yl)-2-oxo-2,3-dihydro-1H-indol-3-yl]acetic acid from example 1.6 in 10 ml of dimethylformamide. The mixture was stirred for 15 minutes and then 285 mg (1.56 mmol) of 1-methyl-4-piperidin-4-ylpiperazine and 1.03 ml (7.41 mmol) of triethylamine were added. The reaction mixture was stirred at room temperature overnight. The reaction was checked by TLC (silica gel, dichloromethane/methanol 15:5). The reaction mixture was mixed with water and diluted with ethyl acetate. The phases were separated and the aqueous phase was extracted with ethyl acetate (1×). The combined organic phase was washed with water (1×) and saturated sodium chloride solution (1×), dried over magnesium sulfate and filtered, and the solvent was evaporated in vacuo. The resulting residue was purified by preparative MPLC (ISCO Companion, 12 g NP cartridge) with dichloromethane/methanol (10-70%) as eluent. 497 mg (0.99 mmol, 66%) of the title compound were obtained as a colorless solid.

ESI-MS [M+H$^+$]=503 Calculated for $C_{28}H_{34}N_6O_3$=502.62

1.8 1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile, Trifluoroacetic Acid Salt 6.6 mg (0.19 mmol) of sodium hydride and, after 10 minutes, 24 L (0.19 mmol) of phenylsulfonyl chloride were added to a solution, cooled to 0° C., of 80.0 mg (0.16 mmol) of 3-(2-ethoxypyridin-3-yl)-3-{2-[4-(4-methylpiperazin-1-yl)piperidin-1-yl]-2-oxoethyl}-2-oxoindoline-5-carbonitrile from example 1.7 in 2 ml of dimethylformamide. The reaction mixture was allowed to warm to room temperature and was stirred for 30 minutes. The progress of the reaction was followed by thin-layer chromatography (silica gel, dichloromethane/methanol 1:1). Saturated sodium bicarbonate solution and ethyl acetate were added to the reaction mixture. The two phases were then separated and the aqueous phase was extracted once more with ethyl acetate (1×). The combined organic phase was washed with water (1×) and with saturated sodium chloride solution (1×), dried over magnesium sulfate and filtered, and the solvent was evaporated in vacuo. The residue was purified by preparative HPLC (RP, eluent acetonitrile/water, 0.01% TFA). 54.4 mg (0.08 mmol, 51%, 95% purity) of the title compound were obtained as a colorless solid.

ESI-MS [M+H$^+$]=643 Calculated for $C_{34}H_{38}ClN_6O_5S$=642.78

The compounds of the formula I according to examples 2 to 9 can be prepared using the appropriate starting compounds in analogy to the process for preparing example 1.

The compounds I of the invention can be purified for example by crystallization, conventional normal-phase column chromatography (such as, for example, NP SiO$_2$ cartridge, Chromabond and dichloromethane/methanol as eluent) and/or by preparative HPLC (RP, eluent acetonitrile/water, 0.1% TFA or 0.1% acetic acid). Compounds I then result as trifluoroacetic acid salt or acetic acid salt.

Example 2

(±)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile Trifluoroacetic Acid Salt (compound I-37)

ESI-MS [M+H$^+$]=717 Calculated for $C_{37}H_{44}ClN_6O_7S$=716.86

Example 3

(±)-1-Phenylsulfonyl-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile, Trifluoroacetic Acid Salt (Compound I-40)

ESI-MS [M+H$^+$]=657 Calculated for $C_{35}H_{40}ClN_6O_5S$=656.81

Example 4

(±)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile, Trifluoroacetic Acid Salt (Compound I-38)

ESI-MS [M+H$^+$]=687 Calculated for $C_{36}H_{42}ClN_6O_6S$=686.84

Example 5

(±)-3-(2-Ethoxypyridin-3-yl)-1-(2-methoxyphenylsulfonyl)-3-{2-[4-(4-methylpiperazin-1-yl)-piperidin-1-yl]-2-oxoethyl}-2-oxo-2,3-dihydro-1H-indole-5-carbonitrile, Trifluoroacetic Acid (Compound I-32)

ESI-MS [M+H$^+$]=673 Calculated for $C_{35}H_{40}ClN_6O_6S$=672.81

Example 6

(±)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile, Trifluoroacetic Acid Salt (Compound I-31)

ESI-MS [M+H$^+$]=703 Calculated for $C_{36}H_{42}N_6O_7S$=702.84

Example 7

(±)-1-Phenylsulfonyl-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile, Trifluoroacetic Acid Salt (Compound I-4)

ESI-MS [M+H$^+$]=643 Calculated for $C_{34}H_{38}ClN_6O_5S$=642.78

Example 8

(±)-3-(2-Ethoxypyridin-3-yl)-1-(2-methoxyphenylsulfonyl)-3-{2-[4-(1-methylpiperidin-4-yl)-piperazin-1-yl]-2-oxoethyl}-2-oxo-2,3-dihydro-1H-indole-5-carbonitrile, Trifluoroacetic Acid Salt (Compound I-2)

ESI-MS [M+H$^+$]=673 Calculated for $C_{35}H_{40}ClN_6O_6S$=672.81

Example 9

(±)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile, Trifluoroacetic Acid Salt (Compound I-1)

ESI-MS [M+H$^+$]=703 Calculated for $C_{36}H_{42}ClN_6O_7S$=702.84

III. Preparation of Chiral Compounds of the General Formula I

Racemic compounds of the formula I can be resolved for example by separation on a preparative chiral column.

Example 2A and Example 2B

Racemate resolution of (±)-1-(2,4-dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile, Trifluoroacetic Acid Salt (Compound I-37)

219 mg of (±)-1-(2,4-dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile, trifluoroacetic acid salt from example 2 were separated on a preparative chiral column (Chiralcell OD, flow rate 55 ml/min) with n-heptane/ethanol (7:3) as eluent. 41 mg of the enantiomer which eluted first and had positive rotation (example 2A) and 25 mg of the enantiomer which eluted later and had negative rotation (example 2B) were obtained.

Example 2A (+)-(2,4-Dimethoxyphenylsulfonyl)-3-(2-ethoxypyridin-3-yl)-3-{2-[4-(4-ethylpiperazin-1-yl)-piperidin-1-yl]-2-oxoethyl}-2-oxo-2,3-dihydro-1H-indole-5-carbonitrile (Compound I-37A)

ESI-MS [M+H$^+$]=717
HPLC (Chiralcel OD 0.46 cm×25 cm; n-heptane/ethanol 7:3) R$_t$=11.1 min
$[\alpha]^{20}_D$=+13 (c 0.1, CHCl$_3$)

¹H-NMR ([d₆]-DMSO, 500 MHz) δ[ppm]=8.10 (1H), 7.95 (2H), 7.85 (1H), 7.80 (1H), 7.60 (1H), 7.00 (1H), 6.65 (2H), 4.10 (2H), 3.80-4.05 (6H), 3.60 (3H), 3.15-3.30 (1H), 2.90 (1H), 2.25-2.45 (11H), 1.70 (1H), 1.55 (1H), 1.25 (2H), 1.00-1.10 (3H), 0.98 (3H), 0.80 (1H).

Example 2B (−)-(2,4-Dimethoxyphenylsulfonyl)-3-(2-ethoxypyridin-3-yl)-3-{2-[4-(4-ethylpiperazin-1-yl)-piperidin-1-yl]-2-oxoethyl}-2-oxo-2,3-dihydro-1H-indole-5-carbonitrile (Compound I-37B)

ESI-MS [M+H⁺]=717
HPLC (Chiralcel OD 0.46 cm×25 cm; n-heptane/ethanol 7:3) $R_f$=15.9 min
$[α]_{20}^D$=−14 (c 0.1, CHCl₃)
¹H-NMR ([d₆]-DMSO, 500 MHz) δ[ppm]=8.10 (1H), 7.95 (2H), 7.85 (1H), 7.80 (1H), 7.60 (1H), 7.00 (1H), 6.65 (2H), 4.10 (2H), 3.80-4.05 (6H), 3.60 (3H), 3.15-3.30 (1H), 2.90 (1H), 2.25-2.45 (11H), 1.70 (1H), 1.55 (1H), 1.25 (2H), 1.00-1.10 (3H), 0.98 (3H), 0.80 (1H).

Example 6A and Example 6B

Racemate Resolution of 1-(2,4-dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile, Trifluoroacetic Acid Salt (Compound I-31)

200 mg of (±)-1-(2,4-dimethoxyphenylsulfonyl)-3-(2-ethoxypyridin-3-yl)-3-{2-[4-(4-methyl-piperazin-1-yl)piperidin-1-yl]-2-oxoethyl}-2-oxo-2,3-dihydro-1H-indole-5-carbonitrile, trifluoroacetic acid salt from example 6 were separated on a preparative chiral column (Chiralcell OD, flow rate 55 ml/min) with n-heptane/ethanol (7:3) as eluent. 13 mg of the enantiomer which eluted first and had positive rotation (example 6A) and 9 mg of the enantiomer which eluted later and had negative rotation (example 6B) were obtained.

Example 6A (+)1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile (Compound I-31A)

ESI-MS [M+H⁺]=703
HPLC (Chiralcel OD 0.46 cm×25 cm; n-heptane/ethanol 7:3) $R_f$=12.9 min
$[α]_{20}^D$=+13 (c 0.1, CHCl₃)
¹H-NMR ([d₆]-DMSO, 500 MHz) δ[ppm]=8.10 (1H), 7.95 (2H), 7.85 (1H), 7.80 (1H), 7.55-7.60 (1H), 7.05 (1H), 6.65 (2H), 4.10 (2H), 3.80-4.05 (6H), 3.60 (3H), 3.15-3.30 (1H), 2.90 (1H), 2.25-2.50 (9H), 2.15 (3H), 1.70 (1H), 1.55 (1H), 1.20 (2H), 1.05 (3H), 0.80 (1H).

Example 6B (−)1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile (Compound I-31B)

ESI-MS [M+H⁺]=703
HPLC (Chiralcel OD 0.46 cm×25 cm; n-heptane/ethanol 7:3) $R_f$=17.3 min
¹H-NMR ([d₆]-DMSO, 500 MHz) δ[ppm]=8.10 (1H), 7.95 (2H), 7.85 (1H), 7.80 (1H), 7.55-7.60 (1H), 7.05 (1H), 6.65 (2H), 4.10 (2H), 3.80-4.05 (6H), 3.60 (3H), 3.15-3.30 (1H), 2.90 (1H), 2.25-2.50 (9H), 2.15 (3H), 1.70 (1H), 1.55 (1H), 1.20 (2H), 1.05 (3H), 0.80 (1H).

Example 9A and Example 9B

Racemate resolution of 1-(2,4-dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile, Trifluoroacetic Acid Salt (Compound I-1)

200 mg of (±)-1-(2,4-dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile, trifluoroacetic acid salt from example 9 were separated on a preparative chiral column (Chiralcell OD, flow rate 55 ml/min) with n-heptane/ethanol (7:3) as eluent. 41 mg of the enantiomer which eluted first and had positive rotation (example 9A) and 23 mg of the enantiomer which eluted later and had negative rotation (example 9B).

Example 9A (+)1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile (Compound I-1A)

ESI-MS [M+H⁺]=703
HPLC (Chiralcel OD 0.46 cm×25 cm; n-heptane/ethanol 7:3) $R_f$=17.1 min
$[α]_{20}^D$=+9 (c 0.1, CHCl₃)
¹H-NMR ([d₆]-DMSO, 500 MHz) δ[ppm]=8.10 (1H), 7.95 (2H), 7.85 (1H), 7.80 (1H), 7.60 (1H), 7.05 (1H), 6.65 (2H), 4.10 (2H), 3.90 (1H), 3.85 (3H), 3.60 (3H), 3.45 (2H), 3.25 (1H), 3.10 (1H), 3.00 (1H), 2.75 (2H), 2.40 (2H), 2.05-2.25 (6H), 1.80 (2H), 1.65 (2H), 1.40 (2H), 1.05 (3H).

Example 9B (−)1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile (Compound I-1B)

ESI-MS [M+H⁺]=703
HPLC (Chiralcel OD 0.46 cm×25 cm; n-heptane/ethanol 7:3) $R_f$=26.3 min
$[α]_{20}^D$=−14 (c 0.1, CHCl₃)
¹H-NMR ([d₆]-DMSO, 500 MHz) δ[ppm]=8.10 (1H), 7.95 (2H), 7.85 (1H), 7.80 (1H), 7.60 (1H), 7.05 (1H), 6.65 (2H), 4.10 (2H), 3.90 (1H), 3.85 (3H), 3.60 (3H), 3.45 (2H), 3.25 (1H), 3.10 (1H), 3.00 (1H), 2.75 (2H), 2.40 (2H), 2.05-2.25 (6H), 1.80 (2H), 1.65 (2H), 1.40 (2H), 1.05 (3H).

Example 10B (−)1-(2,4-Dimethoxyphenylsulfonyl)-3-(2-ethoxypyridin-3-yl)-3-{2-[4-(1-ethylpiperidin-4-yl)-piperazin-1-yl]-2-oxoethyl}-2-oxo-2,3-dihydro-1H-indole-5-carbonitrile (Compound I-7B)

Example 10B was prepared in analogy to example 9B using 1-(1-ethylpiperidin-4-yl)piperazine instead of 1-(1-methylpiperidin-4-yl)piperazine as amine X.
ESI-MS [M+H$^+$]=717

Example 11B 1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile (Compound I-61B)

Example 11B can be prepared in analogy to example 9B using 1-methyl[4,4']bipiperidine instead of 1-(1-methylpiperidin-4-yl)piperazine as amine X.
ESI-MS [M+H$^+$]=702

IV. Determination of the Biological Activity

1. Vasopressin V1b Receptor Binding Assay:
Substances:
The test substances were dissolved in a concentration of $10^{-2}$ M in DMSO and further diluted to $5 \times 10^{-4}$ M to $5 \times 10^{-9}$ M. These serial DMSO predilutions were diluted 1:10 with assay buffer. The substance concentration was further diluted 1:5 in the assay mixture (2% DMSO in the mixture).
Membrane Preparation:
CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.
Binding Assay:
The binding assay was carried out by the method based on that of Tahara et al. (Tahara A et al., Brit. J. Pharmacol. 125, 1463-1470 (1998)).
The incubation buffer was: 50 mM Tris, 10 mM MgCl$_2$, 0.1% BSA, pH 7.4.
In the assay mixture (250 µl), membranes (50 µg/ml protein in incubation buffer) from CHO-K1 cells with stably expressed human V1b receptors (cell line hV1b__3H2_CHO) were incubated with 1.5 nM $^3$H-AVP (8-Arg-vasopressin, PerkinElmer #18479) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 M AVP (Bachem # H1780). All determinations were carried out as triplicate determinations. After incubation (60 minutes at room temperature), the free radioligand was filtered off by vacuum filtration (Skatron cell harvester 7000) through Wathman GF/B glass fiber filter mats, and the filters were transferred into scintillation vials. The liquid scintillation measurement took place in a model 2000 or 2200CA Tricarb instrument (Packard). Conversion of the measured cpm into dpm was carried out with the aid of a standard quench series.
Analysis:
The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.
2. Vasopressin V1a Receptor Binding Assay:
Substances:
The test substances were dissolved in a concentration of $10^{-2}$ M in DMSO. Further dilution of these DMSO solutions took place in incubation buffer (50 mM Tris, 10 mM MgCl$_2$, 0.1% BSA, pH 7.4).
Membrane Preparation:
CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.
Binding Assay:
The binding assay was carried out by the method based on that of Tahara et al. (Tahara A et al., Brit. J. Pharmacol. 125, 1463-1470 (1998)).
The incubation buffer was: 50 mM Tris, 10 mM MgCl$_2$, 0.1% BSA, pH 7.4.
In the assay mixture (250 µl), membranes (20 µg/ml protein in incubation buffer) from CHO-K1 cells with stably expressed human V1a receptors (cell line hV1a__5_CHO) were incubated with 0.04 nM $^{125}$I-AVP (8-Arg-vasopressin, NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out. After incubation (60 minutes at room temperature), the free radioligand was filtered off by vacuum filtration (Skatron cell harvester 7000) through Wathman GF/B glass fiber filter mats, and the filters were transferred into scintillation vials.
The liquid scintillation measurement took place in a model 2000 or 2200CA Tricarb instrument (Packard). Conversion of the measured cpm into dpm was carried out with the aid of a standard quench series.
Analysis:
The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.
3. Vasopressin V2 Receptor Binding Assay:
Substances:
The test substances were dissolved in a concentration of $10^{-2}$ M in DMSO. Further dilution of these DMSO solutions took place in incubation buffer (50 mM Tris, 10 mM MgCl$_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (250 µl), membranes (50 µg/ml protein in incubation buffer) from CHO-K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out.

After incubation (60 minutes at room temperature), the free radioligand was filtered off by vacuum filtration (Skatron cell harvester 7000) through Wathman GF/B glass fiber filter mats, and the filters were transferred into scintillation vials.

The liquid scintillation measurement took place in a model 2000 or 2200CA Tricarb instrument (Packard). Conversion of the measured cpm into dpm was carried out with the aid of a standard quench series.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki.

4. Oxytocin Receptor Binding Assay

Substances:

The substances were dissolved in a concentration of $10^{-2}$ M in DMSO and diluted with incubation buffer (50 mM Tris, 10 mM $MgCl_2$, 0.1% BSA, pH 7.4).

Cell Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. The lyzed cells were then centrifuged at 750×g at 4° C. for 20 minutes, the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to 5×$10^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Triplicate determinations were set up. Bound and free radioligand were separated by filtration under vacuum with Whatman GF/B glass fiber filters with the aid of a Skatron cell harvester 7000. The bound radioactivity was determined by liquid scintillation measurement in a Tricarb Beta counter, model 2000 or 2200CA (Packard).

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant hOT receptors is 7.6 nM and was used to determine the Ki.

5. Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln2/T½ (content of microsomal protein in mg/ml)×1000 [ml/min/mg] (modified from references: Di, The Society for Bimolecular Screening, 2003, 453-462; Obach, D M D, 1999 vol 27. N 11, 1350-1359).

6. Methods for In Vitro Determination of the Cytochrome P450 (CYP) Inhibition

Luminescent Substrates for 2C9 and 3A4:

0.4 mg/ml human liver microsomes are preincubated with the test substances to be investigated (0-20 µM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-Dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 µM (or 50 µM) test substance in 50 mM potassium phosphate buffer for 5 min. The reaction is started with NADPH. After 30 min 4 µM midazolam (final concentration) are added, and incubation is continued for 10 min. 75 µl of the reaction solution are removed after 10 min, and stopped with 150 µl of acetonitrile solution.

Coincubation:

0.05 mg/ml microsomal protein (human liver microsomes) are preincubated with 4 µm midazolam (final concentration) and 0-10 µM (or 50 µM) test substance in 50 mM potassium phosphate buffer for 5 min. The reaction is started with NADPH. 75 μl of the reaction solution are removed after 10 min and stopped with 150 μl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

7. Method for Determining the Solubility in Water (in mg/ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

8. Results

The results of the receptor binding investigations are expressed as receptor binding constants [$K_i$(V1b), $K_i$(V1a), $K_i$(V2), $K_i$(OT)]. The results of the investigation of the metabolic stability are indicated as microsomal clearance (mCl).

The compounds of the invention show very high affinities for the V1b receptor in these assays (maximally 300 nM, or maximally 30 nM, frequently <3 nM). The compounds also show high selectivities vis-à-vis the V1a receptor. In addition, they have a good metabolic stability, measured as microsomal clearance.

The results are listed in table 2. The numbers of the compounds refer to the synthesis examples.

TABLE 2

| Example | $K_i$(h-V1b)* [nM] | $K_i$(h-V1a)/ $K_i$(h-V1b)* | Human microsomal clearance [μl min$^{-1}$ mg$^{-1}$] |
|---|---|---|---|
| 1 | ++ | ++ | +++ |
| 2 | +++ | +++ | +++ |
| 3 | ++ | +++ | +++ |
| 4 | ++ | +++ | ++ |
| 5 | ++ | ++ | ++ |
| 6 | +++ | +++ | +++ |
| 7 | ++ | +++ | +++ |
| 8 | ++ | +++ | +++ |
| 9 | +++ | +++ | +++ |
| 10B | +++ | +++ | +++ |

*h = human

Key:

| | $K_i$(V1b) | $K_i$(h-V1a)/ $K_i$(h-V1b) | Human microsomal clearance |
|---|---|---|---|
| + | 300->30 nM | 10-<15 | >200-300 μl min$^{-1}$ mg$^{-1}$ |
| ++ | 3-30 nM | 15-30 | 100-200 μl min$^{-1}$ mg$^{-1}$ |
| +++ | <3 nM | >30 | <100 μl min$^{-1}$ mg$^{-1}$ |

The invention claimed is:

1. A compound of the formula I

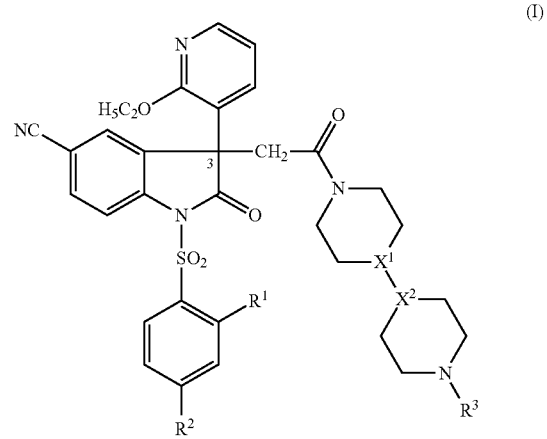

in which
R$^1$ is hydrogen, methoxy or ethoxy;
R$^2$ is hydrogen or methoxy;
R$^3$ is hydrogen, methyl, ethyl, n-propyl or isopropyl;
X$^1$ and X$^2$ are N or CH, with the proviso that X$^1$ and X$^2$ are not simultaneously N;
a racemate, or an enantiomer, or a pharmaceutically acceptable salt thereof.

2. A compound of claim 1, in which R$^1$ is hydrogen or methoxy.

3. A compound of claim 1, in which R$^3$ is hydrogen, methyl or ethyl.

4. A compound of claim 1, in which X$^1$ is N and X$^2$ is CH.

5. A compound of claim 1, in which X$^1$ is CH and X$^2$ is N.

6. A compound of claim 1, in which
R$^1$ is methoxy;
R$^2$ is methoxy;
R$^3$ is methyl;
X$^1$ is CH; and
X$^2$ is N.

7. A compound of claim 1, in which
R$^1$ is methoxy;
R$^2$ is methoxy;
R$^3$ is methyl;
X$^1$ is N; and
X$^2$ is CH.

8. A compound of claim 1, in which
R$^1$ is methoxy;
R$^2$ is methoxy;
R$^3$ is methyl;
X$^1$ is CH; and
X$^2$ is CH.

9. A compound of claim 1, in which
R$^1$ is methoxy;
R$^2$ is methoxy;
R$^3$ is ethyl;
X$^1$ is CH; and
X$^2$ is N.

10. A compound of claim 1, in which
R$^1$ is methoxy;
R$^2$ is methoxy;
R$^3$ is ethyl;
X$^1$ is N; and
X$^2$ is CH.

11. A compound of claim 1, where the (−) enantiomer has an enantiomeric purity of at least 90% enantiomeric excess (ee).

12. A compound according to claim 1, or a pharmaceutically acceptable salt thereof, selected from the group consisting of:

(±)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile;

(+)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile;

(−)-1-(2,4-Dimethoxyphenylsulfonyl)-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile;

(±)-3-(2-Ethoxypyridin-3-yl)-1-(2-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(+)-3-(2-Ethoxypyridin-3-yl)-1-(2-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(−)-3-(2-Ethoxypyridin-3-yl)-1-(2-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(±)-1-Phenylsulfonyl-3-(2-ethoxypyridin-3-yl)-3-{2-[4-(1-methylpiperidin-4yl)piperazin-1-yl]-2-oxoethyl}-2-oxo-2,3-dihydro-1H-indole-5-carbonitrile;

(+)-1-Phenylsulfonyl-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile;

(−)-1-Phenylsulfonyl-3-(2-ethoxypyridin-3-yl)-3-{2-[4-(1-methylpiperidin-4-yl)piperazin-1-yl]-2-oxoethyl}-2-oxo-2,3-dihydro-1H-indole-5-carbonitrile;

(±)-3-(2-Ethoxypyridin-3-yl)-1-(4-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(+)-3-(2-Ethoxypyridin-3-yl)-1-(4-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(−)-3-(2-Ethoxypyridin-3-yl)-1-(4-methoxyphenylsulfonyl)-3-{2-[4-(1-methylpiperidin-4-yl)piperazin-1-yl]-2-oxoethyl}-2-oxo-2,3-dihydro-1H-indole-5-carbonitrile;

(±)-1-(2,4-Dimethoxyphenylsulfonyl)-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(+)-1-(2,4-Dimethoxyphenylsulfonyl)-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(−)-1-(2,4-Dimethoxyphenylsulfonyl)-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(±)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile;

(+)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile;

(−)-3-(2-Ethoxypyridin-3-yl)-3-{2-[4-(1-ethylpiperidin-4-yl)piperazin-1-yl]-2-oxoethyl}-1-(2-methoxyphenylsulfonyl)-2-oxo-2,3-dihydro-1H-indole-5-carbonitrile;

(±)-1-Phenylsulfonyl-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(+)-1-Phenylsulfonyl-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(−)-1-Phenylsulfonyl-3-(2-ethoxypyridin-3-yl)-3-{2-[4-(1-ethylpiperidin-4-yl)piperazin-1-yl]-2-oxoethyl}-2-oxo-2,3-dihydro-1H-indole-5-carbonitrile;

(±)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile;

(+)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile;

(−)-3-(2-Ethoxypyridin-3-yl)-3-{2-[4-(1-ethylpiperidin-4-yl)piperazin-1-yl]-2-oxoethyl}-1-(4-methoxyphenylsulfonyl)-2-oxo-2,3-dihydro-1H-indole-5-carbonitrile;

(±)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(+)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(−)-1-(2,4-Dimethoxyphenylsulfonyl)-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(±)-3-(2-Ethoxypyridin-3-yl)-1-(2-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(+)-3-(2-Ethoxypyridin-3-yl)-1-(2-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(−)-3-(2-Ethoxypyridin-3-yl)-1-(2-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(±)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(+)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(−)-1-Phenylsulfonyl-3-(2-ethoxypyridin-3-yl)-3-{2-[4-(4-methylpiperazin-1-yl)piperidin-1-yl]-2-oxoethyl}-2-oxo-2,3-dihydro-1H-indole-5-carbonitrile;

(±)-3-(2-Ethoxypyridin-3-yl)-1-(4-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(+)-3-(2-Ethoxypyridin-3-yl)-1-(4-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(−)-3-(2-Ethoxypyridin-3-yl)-1-(4-methoxyphenylsulfonyl)-3-{2-[4-(4-methylpiperazin-1-yl)piperidin-1-yl]-2-oxoethyl}-2-oxo-2,3-dihydro-1H-indole-5-carbonitrile;

(±)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(+)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(−)-1-(2,4-Dimethoxyphenylsulfonyl)-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(±)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile;

(+)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile;

(−)-3-(2-Ethoxypyridin-3-yl)-3-{2-[4-(4-ethylpiperazin-1-yl)piperidin-1-yl]-2-oxoethyl}-1-(2-methoxyphenylsulfonyl)-2-oxo-2,3-dihydro-1H-indole-5-carbonitrile;

(±)-1-Phenylsulfonyl-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(+)-1-Phenylsulfonyl-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(−)-1-Phenylsulfonyl-3-(2-ethoxypyridin-3-yl)-3-{2-[4-(4-ethylpiperazin-1-yl)piperidin-1-yl]-2-oxoethyl}-2-oxo-2,3-dihydro-1H-indole-5-carbonitrile;

(±)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile;

(+)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile;

(−)-3-(2-Ethoxypyridin-3-yl)-3-{2-[4-(4-ethylpiperazin-1-yl)piperidin-1-yl]-2-oxoethyl}-1-(4-methoxyphenylsulfonyl)-2-oxo-2,3-dihydro-1H-indole-5-carbonitrile;

(±)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile;

(+)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile; and (−)-1-(2,4-Dimethoxyphenylsulfonyl)-3-(2-ethoxypyridin-3-yl)-3-[2-(1'-methyl-[4,4']bipiperidinyl-1-yl)-2-oxoethyl]-2-oxo-2,3-dihydro-1H-indole-5-carbonitrile.

13. A method for the treatment of a disease selected from the group consisting of arterial hypertension and congestive heart failure (CHF), the method comprising administering a compound of claim 1 or a pharmaceutically acceptable salt thereof to a subject in need thereof.

14. A pharmaceutical composition comprising a compound of claim 1, or a pharmaceutically acceptable salt thereof, and a pharmaceutically acceptable carrier.

* * * * *